United States Patent [19]

Gustafson et al.

[11] Patent Number: 5,196,524
[45] Date of Patent: Mar. 23, 1993

[54] FUSION REPORTER GENE FOR BACTERIAL LUCIFERASE

[75] Inventors: Gary D. Gustafson; Thomas D. Ingolia, both of Indianapolis; Gretchen Kirchner, Jeffersonville; Jean L. Roberts, Indianapolis, all of Ind.

[73] Assignee: Eli Lilly and Company, Indianapolis, Ind.

[21] Appl. No.: 294,170

[22] Filed: Jan. 6, 1989

[51] Int. Cl.$^5$ .............................................. C12N 15/00
[52] U.S. Cl. ................................... 536/23.2; 435/69.1; 435/320.1; 435/8; 435/25; 530/350; 930/200; 930/240; 935/14; 935/47; 935/90
[58] Field of Search ...................... 424/94.4; 435/69.7, 435/8, 189; 935/78, 47

[56] References Cited

U.S. PATENT DOCUMENTS 4,581,335  4/1986  Baldwin ........................... 435/172.3
4,840,896  6/1989  Reddy et al. ......................... 435/68

OTHER PUBLICATIONS

Olsson et al. Molecular Gen. Genet. (1988) 215:1-9 "The Use of the luxA gene of the bacterial".
Ulmer Science 219:666-671 Protein Engineering.
Cohn et al. Journal of Biological Chemistry (1985) 260 10:6139-6146 Nucleotide Seq. of the luxA gene of Vharveyi . . .
Johnson et al. Journal of Biological Chemistry (1986) 261 11:4805-4811 Nucleotide Seq. of the luxB gene of Vharveyi.
Bergey's Manual of Systematic Bacteriology, Krieg, ed. Williams & Wilkins, Baltimore & London, pp. 529, 532, 533.
Seliger et al., 1960, Archives of Biochemistry and Biophysics, (88), 136–141.
McKenney et al., 1981, Gene Amplification and Analysis, (2), 383–415.
Chater et al., 1982, Gene, (19), 21–32.
Rosenberg et al., 1983, Studying Promoters and Terminators by Gene Fusion, (222), 734–739.
Engebrecht et al., 1985, Science, (227) 1345–1347.
Cohn et al., 1985, The Journal of Biological Chemistry, (260):10, 6139–6146.
Johnston et al., 1986, The Journal of Biological Chemistry, (261):11, 4805–4811.
Ow et al., 1986, Science (234), 856–859.
Legocki et al., 1986, Proc. Natl. Acad. Sci., (83), 9080–9084.
Ow et al., 1987, Proc. Natl. Acad. Sci., (84), 4870–4874.
Schauer et al., 1988, Science, (240), 768–772.

*Primary Examiner*—Robert A. Wax
*Assistant Examiner*—T. Nisbet
*Attorney, Agent, or Firm*—John E. Parrish; Robert A. Conrad; Leroy Whitaker

[57] ABSTRACT

Novel fusion reporter genes, fusion reporter proteins, and an improved reporter system for measuring the relative activity of a promoter sequence. A luxAB fusion gene of the present invention is particularly useful as a reporter gene and is derived from the fusion of a luxA gene and a luxB gene from Vibrio harveyi. The gene products of the luxA and luxB genes are the α- and β-subunits, respectively, of a bacterial luciferase. A fusion protein encoded by a luxAB fusion gene is a single active protein and is particularly useful as a reporter protein having luciferase activity. An advantage of such a reporter system to assay gene expression in many cells which contain $FMNH_2$, such as bacterial and yeast cells, is that an immediate and quantitative assessment of gene expression may be made from real-time light measurements using intact cells.

24 Claims, 16 Drawing Sheets

FUSION REPORTER GENE FOR BACTERIAL LUCIFERASE

BACKGROUND OF THE INVENTION

The present invention relates to the preparation of a single active protein from a novel fusion gene for use as a reporter gene system. More specifically, this invention relates to the fusion of a luxA and luxB gene from *Vibrio harveyi* so as to produce a fused lux AB gene which is useful as a reporter gene. The fusion gene encodes a single active fusion protein as its gene product, which is useful as a reporter protein.

It is generally recognized that gene expression studies will benefit from the use of a reporter gene. An ideal reporter gene is easily assayed, both in vivo and in vitro, and is able to indicate the temporal and spatial aspects of gene expression. Optimally, the reporter gene encodes a gene product whose activity is not normally found in the organism of interest and thus may be easily assayed.

A problem of considerable importance in genetic engineering technology is the difficulty of obtaining a promotor sequence that promotes the expression of genes in a host organism. A reporter gene may be fused to a promoter of intersest and the amount of reporter gene product produced is indicative of the relative activity of the promoter. A good example of such a reporter gene is β-galactosidase, an enzyme encoded by the lac Z gene of *E. coli*. The presence of the lac Z gene product in a cell can be qualitatively determined in whole cells and can be quantitatively measured in cell-free extracts.

An ideal candidate for a reporter gene is the luxA and luxB luciferase gene system from *Vibrio harveyi*. The gene product of the luxA gene is the α subunit of the enzyme and the gene product of the luxB gene is the β submit of the enzyme. The α- and β-subunits encoded by the luxA and luxB genes respectively, form a functionally active heterodimer protein enzyme complex which in the presence of substrates will emit light.

Bacterial luciferase, as exemplified by luciferase derived from *Vibrio harveyi* (EC 1.14.14.3, alkanol reduced-FMN-oxygen oxidoreductase; 1-hydroxylating, luminescing), is a mixed function oxidase, formed by the association of two different protein subunits α and β. The α-subunit has an apparent molecular weight of ~42,000 d. and the β-subunit has an apparent molecular weight of ~37,000 d. Cohn et al., 1983, Proc. Acad. Sci. USA 80: 102–123. The α- and β-subunits must associate to form a 2-chain complex in order to generate functional luciferase enzyme, which catalyzes the light emitting reaction of naturally bioluminescent bacteria, such as *Vibrio harveyi* (U.S. Pat. No. 4,581,335; Belas et al. 1982, Science 218:791-793), *Vibrio fischeri* (Engebracht et al., 1983, Cell 32:773-781; Engebrecht and Silverman, 1984, Proc. Natl. Acad. Sci. U.S.A. 81:4154–4158) and other marine bacteria. Specifically, bacterial luciferase catalyzes the flavin-mediated hydroxylation of a long-chain aldehyde to yield carboxylic acid and an excited flavin; the flavin decays to ground state with the concomitant emission of blue green light (λmax=490 nm). Legocki et al., 1986, Proc. Nat. Acad. Sci. USA 81:9080.

The reaction in vitro is initiated by injection of reduced flavin mononucleotide (FMNH₂) into a vial containing bacterial luciferase, oxygen, and a long-chain aldehyde, usually n-decyl aldehyde. U.S. Pat. No. 4,581,335. The reaction pathway is as follows:

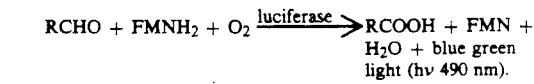

$$RCHO + FMNH_2 + O_2 \xrightarrow{luciferase} RCOOH + FMN + H_2O + \text{blue green light } (h\nu\ 490\ nm).$$

The number of photons produced in the reaction is proportional to the amount of protein enzyme present when substrates are in excess. Since flavin mononucleotide (FMN) is a normal constituent of most cells and n-decyl aldehyde freely crosses membranes, the product of the luxA and lux B genes can be quantitatively measured in intact FMN-containing cells.

A different luciferase enzyme system is found in the firefly, *Photinus pyradis*. Firefly luciferase (EC 1.13.12.7, luciferin: oxygen 4-oxidoreductase; decarboxylating, ATP hydrolysing) has an apparent molecular weight of ~62,000 d. and requires luciferin, ATP, and O₂ as substrates. Specifically, firefly luciferase catalyzes the light producing, adenosine triphosphate (ATP)-dependent oxidation of luciferin. The reaction pathway catalyzed by firefly luciferase is as follows:

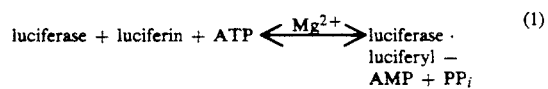

$$\text{luciferase} + \text{luciferin} + ATP \xrightleftharpoons{Mg^{2+}} \text{luciferase} \cdot \text{luciferyl} - AMP + PP_i \quad (1)$$

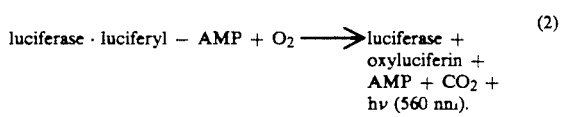

$$\text{luciferase} \cdot \text{luciferyl} - AMP + O_2 \longrightarrow \text{luciferase} + \text{oxyluciferin} + AMP + CO_2 + h\nu\ (560\ nm). \quad (2)$$

Thus, firefly luciferase has an entirely different gene structure, different protein structure, different enzyme activity and reaction pathway as compared with a bacterial luciferase. A required cofactor in this reaction pathway is luciferin, which is a compound that is rarely present in cells other than firefly cells. Since luciferin does not readily cross membranes, it is difficult to use the firefly luciferase system as a reporter system in intact cells. The firefly luciferase gene has been cloned and sequenced (deWet et al., 1985, Proc. Natl. Acad. Sci. 82:7870-7873; deWet et al., 1987, Mol. Cell. Biol. 7:725-737).

The luxA and luxB genes of *Vibrio harveyi* have been cloned (Belas et al., 1982, Science 218: 791-793; Cohn et al. 1983, Proc. Natl. Acad. Sci. USA 80: 120-123) and sequenced (Cohn et al., 1985, J. Biol. Chem. 260: 6139-6146; Johnson et al., 1986, J. Biol. Chem. 261: 4805-4811). The luxA and luxB genes of *Vibrio harveyi* have been used as reporters of gene expression in a filamentous bacterium *Streptomyces coelicolor* (Schauer et al., 1988, Science 240:768-772). One disadvantage to the use of the *Vibrio harveyi* luciferase 2-gene system as a reporter gene system is that it is expressed in bacteria as a polycistronic message from a single promoter. Since eukaryotic cells do not have analogous structures for expression, the use of the *Vibrio harveyi* luciferase gene system in eukaryotic cells is limited. One solution which was utilized in the plant system, so as to overcome this disadvantage, was to fuse a plant promoter to each of the luxA and luxB genes from *Vibrio harveyi* to form two separate transcription-translation cassettes. See Koncz et al., 1987, Proc. Natl. Acad. Sci. USA 84:131. These two cassettes (cassette 1 = T_R-DNA gene 1' promoter luxA; cassette 2 = T_R-DNA gene 2' promoter luxB) containing the luxA and luxB structural genes from *Vibrio harveyi* were introduced into a plant expression vector and transferred into tobacco and carrot cells by Agrobacterium-mediated or direct DNA transformation. Simultaneous expression of the luxA and luxB gene products was monitored by protein immunoblot analysis. Luciferase-mediated light emission in an in vitro assay provided evidence of the assembly of the two protein subunits into a functional dimeric enzyme in plant protoplasts, in transformed calli, and in leaves of transformed plants. However, this method is laborious and is not always feasible due to restrictions imposed by the required plasmid construction.

Several other reporter genes such as β-galactosidase, chloramphenicol acetyltransferase (CAT) and firefly luciferase have been described but may not be advantageous because of their assays for activity or because of difficulties in construction or expression in certain cell types. In particular, the use of firefly luciferase as an in vivo marker is complicated by toxicity and variable access of its substrate to eukaryotic compartments (Ow et al., 1986, Science 234:856-859; deWet et al., 1985, supra). These reporter genes are summarized as follows: β-galactosidase (MacGregor et al., 1987, Somatic Cell Mol. Genet. 13:253-266); galactokinase (e.g., Rosenberg et al., 1983, Science 222:734-739; McKenney et al., 1981, in *Gene Amplification and Analysis*, Volume 2, pp. 383-415, Elsevier/North-Holland, New York); Murooka and Mitani, 1985, J. Biotechnol. 2:303-316; β-glucuronidase (e.g., Jefferson et al., 1986, Proc. Natl. Acad. Sci. 83:8447-8541); human growth hormone (e.g., Seldon et al., 1986, Mol. Cell. Biol. 6:3173-3179); chloramphenicol acetyltransferase (CAT) (e.g., Tsukada, et al., 1987, J. Biol. Chem. 262:8743-8747; Carbonell and Miller, 1987, Appl. Environ. Microbiol. 53:1412-1417; Boulet et al., 1986, Proc. Natl. Acad. Sci. USA 83:3599-3603; Jameson et al., 1986, Endocrinology 119:2560-2567; Montminy et al., 1986, Proc. Natl. Acad. Sci. USA 83:6682-6686); Tn5 neomycin phosphotransferase (e.g., Kaulen et al., 1986, EMBO J. 5:1-8; Simpson et al., 1985, EMBO J. 4:2723-2730) and firefly luciferase (e.g., Ow et al., 1987, Proc. Nat. Acad. Sci. USA 84:4870-4874, Ow et al., 1986, Science 234:856-859).

The present invention represents a significant and distinct contribution to the art in that is provides a means for utilizing the luxA and luxB genes from *Vibrio harveyi* as a reporter gene in a variety of different cell types. The luxA and luxB genes from *Vibrio harveyi* are fused so as to produce a novel fusion gene which encodes single active protein product. Because of the perceived requirement for physical interaction of the α- and β-subunits encoded by the luxA and luxB genes, respectively, in order to generate a functional luciferase enzyme complex having light-producing activity, it was unexpected that a fusion protein which combined the amino acid sequences of the α- and β-subunits on a single polypeptide chain would be functionally active. However, a luxAB fusion gene according to the present invention, when expressed as a fusion protein, surprisingly produces a novel luciferase enzyme that is functionally active both in vitro and in vivo. A fusion protein according to the present invention is a simple and extremely sensitive gene reporter. The luxAB gene of the present invention has been cloned with a variety of expression vectors, suitable for use in bacterial cells, yeast cells, plant cells, animal cells and fungal cells. This protein is an ideal reporter of gene expression in a wide variety of host cells. The activity can be measured in intact, living cells which contain $FMNH_2$, when the volatile substrate decanal is provided. Since many cells do contain $FMNH_2$, a reporter system that comprises a luxAB fusion gene of the present invention allows real-time measurement of gene expression. Because only a single protein (encoded by a single transcriptional unit) need be expressed, utilization of this reporter system in eukaryotic cells is greatly facilitated.

For purposes of the present invention as disclosed and claimed herein, the following terms are as defined below.

α subunit—a polypeptide chain encoded by a luxA gene, which forms an enzyme complex with a β subunit, the enzyme complex having luciferase activity.

β subunit—a polypeptide chain encoded by a luxB gene, which forms an enzyme complex with a α subunit, the enzyme complex having luciferase activity.

Fusion Gene—a DNA sequence comprising two or more genetic sequences (genes or portion of genes) operably linked to one another.

Fusion Protein—a protein encoded by a fusion gene.

luxA—a gene encoding an α-subunit of a bacterial luciferase.

luxB—a gene encoding a β-subunit of a bacterial luciferase.

ori—a plasmid origin of replication.

PGK—the transcriptional and translational activating sequence of the yeast *Saccharomyces cerevisiae* phosphoglycerate kinase gene.

phage—a bacterial virus, also referred to as bacteriophage.

plasmid—an autonomous self-replicating extrachromosomal circular DNA.

Recombinant DNA Cloning Vector—any autonomously replicating agent, including but not limited to plasmids, containing a DNA molecule to which one or more additional DNA segments can or have been added.

Recombinant DNA Expression Vector—any recombinant DNA cloning vector into which one or more transcriptional and translational activator sequence(s) have been incorporated.

Reporter Gene—any genetic material, whose utilization by the transcriptional and/or translational apparatus derived from a cell (e.g., intact cell or cell-free extract) can be monitored, for example, any DNA sequence that is fused to a promoter sequence of interest so as to measure the relative activity of the promoter sequence.

Reporter Protein—a protein encoded by a reporter gene.

Restriction Fragment—any linear DNA molecule generated by the action of one or more restriction enzymes.

Transfectant—a recipient host cell that has undergone transfection.

Transfection—the introduction of DNA into an animal host cell, such as COS-1 cells (may also be termed transformation).

Transformant—a recipient host cell that has undergone transformation.

Transformation—the introduction of DNA into a recipient host cell.

DETAILED DESCRIPTION

Figure 1:
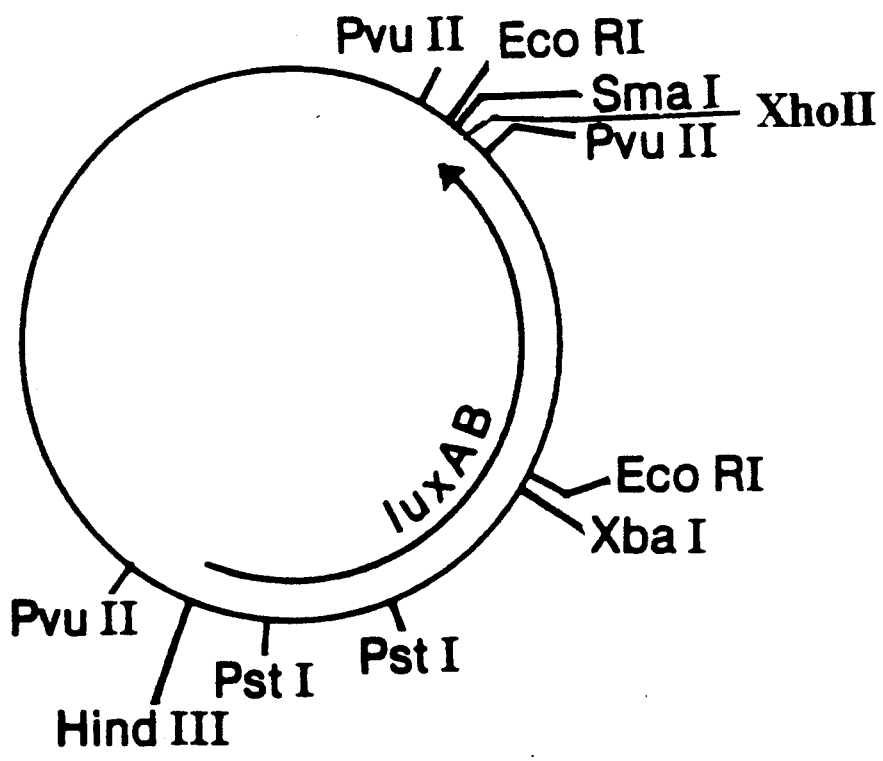
FIG. 1 shows the restriction site and function map of plasmid pIT20.

The present invention comprises novel fusion genes useful as reporter genes, in particular, fusion genes which comprise two DNA sequences, a first DNA sequence which encodes an α-subunit of a bacterial luciferase and a second DNA sequence which encodes a β-subunit of a bacterial luciferase. The first and second DNA sequences are operably linked together to form a fusion gene which encodes a single protein with luciferase enzyme activity. In particular, a luxA and luxB gene have been fused to form a novel luxAB gene. The luxA and luxB gene sequences may be derived from a species of Vibrio bacterium. Preferably, the sequences are derived from *Vibrio harveyi*.

In a particularly preferred embodiment, the luxA and luxB gene sequences are linked together by a third DNA sequence. This third DNA sequence is preferably a restriction enzyme recognition site, most preferably an XbaI site (XbaI=TCTAGA). The 5' to 3' order of the DNA sequences in a particularly preferred embodiment, that is the luxAB fusion gene described herein, is: 5'-luxA-TCTAGA-luxB-3'.

Those skilled in the art will recognize that the luxAB fusion gene is an important part of the present invention. The luxA and luxB genes can be cloned from a Vibrio bacterium, in particular, *Vibrio harveyi*. In addition, the sequence of the luxAB gene can be conventionally synthesized by the modified phosphotriester method using fully protected dioxyribonucleotide building blocks. Such synthetic methods are well known in the art and can be carried out in substantial accordance with the procedure of Itakura et al., 1977, Science 198:1056 and Crea et al., 1978, Proc. Natl. Acad. Sci. USA 75:5765. In addition, an especially preferred method is disclosed in Hsiung et al., 1983, Nucleic Acid Research 11:3227 and Narang et al., 1980, Methods in Enzymology 68:90. In addition to the manual procedures referenced above, the luxAB fusion gene sequence can be synthesized using automated DNA synthesizers, such as the Systec 1450A or Applied Biosystems 380A DNA Synthesizers. Due to the degenerate nature of the genetic code, which results from there being more than one codon for most of the amino acid residues and stop signal, the amino acid residue sequence encoded by the luxAB gene can be encoded by a multitude of different DNA sequences. Because these alternate DNA sequences would encode the same amino acid residue sequence of the present invention, the present invention further comprises these alternate sequence.

In addition, there could be genetic variants of the luxAB gene of the present invention. These genetic variants would share substantial DNA and amino acid residue sequence homology with the fusion genes of the present invention and would have similar, if not identical, activity, but would differ somewhat from the actual fusion genes of the present invention. These genetic variants are also equivalent to the fusion genes of the present invention.

The luxA and luxB genes utilized in the present invention were isolated from a strain of *Vibrio harveyi*. A variety of strains of *Vibrio harveyi* are available from the American Type Culture Collection, Rockville, Md., such as Accession Numbers ATCC 14126 (type strain), ATCC 25919, ATCC 33842, ATCC 33843, ATCC 33866, ATCC 33867, and ATCC 33868. Bacterial luciferase, from *Vibrio harveyi*, is a heterodimer consisting of α and β units that arise from 2 separate genes, luxA and luxB, respectively. In *Vibrio harveyi*, these genes are polycistronic, that is, they are part of a single operon and are transcribed from a single promoter (Belas et al., supra). Since eukaryotic cells are unable to efficiently translate bacterial polycistronic messages, the use of the *Vibrio harveyi* luciferase gene system in eukaryotic cells is limited. The novel fusion gene of the present invention is particularly useful as a reporter gene in a multiplicity of prokaryotic and eukaryotic cell types because it is transcribed as a single protein. Transcription of such a fusion gene as a single unit is a simpler and more reliable indicator of gene expression, and provides an improved reporter gene system. The luxAB luciferase reporter system is an extremely sensitive reporter and allows a real-time measurement of gene expression in intact cells containing $FMNH_2$, when the volatile substrate decanal is provided.

The present invention also encompasses vectors comprising a luxAB fusion reporter gene, and host cells transformed or transfected with such vectors. The invention also comprehends DNA cassettes comprising a promotor sequence operably linked to a luxAB fusion reporter gene.

Plasmid pIT20, as described in Example 1, was prepared and used as a source of a luxAB fusion gene in the construction of expression vectors for bacterial cells (Example 2), yeast cells (Example 3), plant cells (Example 4), animal cells (Example 5), and fungal cells (Example 6). Briefly, a luxAB gene was prepared as follows: a luxA gene, the intercistronic region and a portion of a luxB gene, derived from *Vibrio harveyi*, were subcloned into M13mp19. The intercistronic region, including the translational stop of the luxA gene, was deleted by site-directed mutagenesis and replaced with a 6 bp sequence encoding an XbaI (TCTAGA) recognition site, thereby creating a translational fusion of the luxA and luxB open reading frames. No amino acids were deleted from the luxA or luxB open reading frames, and the only amino acids added were the serine and arginine residues encoded at the XbaI restriction site. In addition to the alteration between the luxA and luxB genes, a HindIII (AAGCTT) recognition site was created by site-directed mutagenesis immediately upstream of the translational start of the luxA gene to facilitate linkage of any prokaryotic or eukaryotic transcriptional and/or translational regulatory sequence (such as any promoter) to the luxAB fusion gene. The desired mutant was identified by hybridization to oligonucleotide probes and sequenced to verify the integrity of the construction. The ~1.2 kb HindIII-EcoRI fragment from the desired M13 construct was purified and then joined to the remainder of the luxAB gene, which was isolated on an ~0.7 kb EcoRI-BglII fragment. The fragments were ligated into plasmid pUC18 to create plasmid pIT20. A restriction site and function map of plasmid pIT 20 is presented in FIG. 1 of the accompanying drawings. *E. coli* cells containing pIT20 were luminescent in the presence of decanal (decyl aldehyde). The light emission could be detected from a liquid culture using a scintillation counter or from colonies on a plate using x-ray film. Light emission was dependent on the presence of the plasmid pIT20 in the *E. coli* cells and on addition of decanal.

Plasmid pIT20 can be isolated from *E. coli* K12 JA221 cells by the procedure described in Example 1. *E. coli* K12 JA221/pIT20 host cells, from which plasmid pIT20 can be isolated, have been deposited and made part of the stock culture collection of the Northern Regional Research Laboratories under Accession Number NRRL B-18301.

Figure 2:
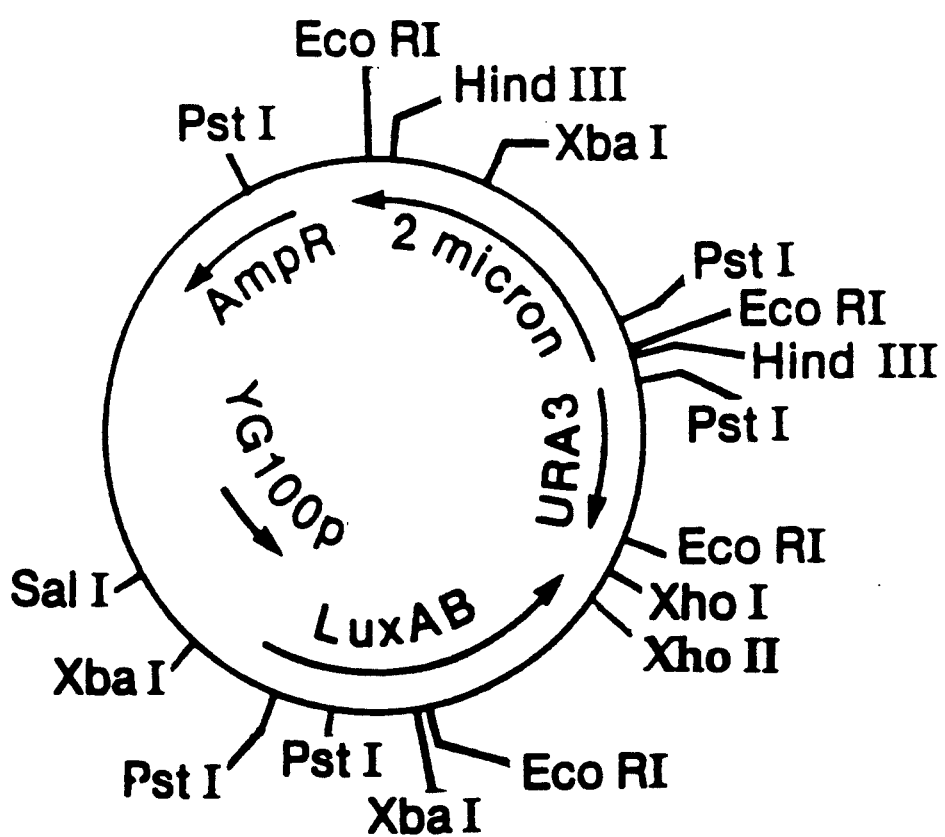
FIG. 2 shows the restriction site and function map of plasmid pIT24.

Plasmid pIT20 was used as a source of a luxAB gene in the construction of plasmid vector pIT24 as described in Example 2. The pIT24 plasmid vector is useful for the expression in *E. coli* of a single polypeptide that is the luxAB gene product. This luxAB fusion protein has functional luciferase activity. Plasmid pIT24 was constructed by ligating an ~2.4 kb HindIII (Klenow-treated)-XhoII fragment from plasmid pIT20 with BamIH (Klenow-treated)-BglII digested plasmid pIT217 DNA. A restriction site and function map of plasmid pIT24 is presented in FIG. 2 of the accompanying drawings.

Plasmid pIT20 was also used as a source of a luxAB gene in the composition of plasmid vector pIT 21 as described in Example 3. This plasmid vector drives expression of a luxAB gene product in yeast cells. Plasmid pIT21 was constructed by ligating the following fragments: (1) an ~7.5 kb SmaI-BglII fragment from plasmid pIT222 containing the yeast phosphoglycerate kinase (PGK) promoter, and a fragment of the yeast 2μ plasmid and yeast URA 3 gene which encode maintenance and selection functions for yeast; (2) an ~1.1 kb HindIII-XbaI fragment from plasmid pIT20 containing a portion of the luxAB gene; (3) an ~1.3 kb PvuII-XbaI fragment from plasmid pIT20 containing a portion of the luxAB gene; and (4) BamHI-HindIII adaptor linkers. A restriction site and function map of plasmid pIT21 is presented in FIG. 7 of the accompanying drawings. Plasmid pIT21 is a yeast expression vector with a luxAB gene and the constitutive PGK yeast promoter, particularly useful as a reporter gene system in yeast cells, such as *Saccharomyces cerevisiae* cells.

Plasmid pIT20 was used as a source of a luxAB gene in the construction of plasmid vector pGAR117 as described in Example 4. This plasmid vector drives expression of a luxAB gene product in plant cells. Plasmid pGAR117 was constructed by ligating an ~2.2 kb KindIII-XhoII fragment from plasmid pIT20 with HindIII (Klenow)-PvuII fragment from plasmid pIT20 with XhoI-digested, Klenow and phosphatase treated plasmid pGAR88. Plasmid pGAR88 (NRRL B-18302) contains the genetic elements necessary for plant cell gene expression. A restriction site and function map of plasmid pGAR117 is presented in FIG. 9 of the accompanying drawings. Plasmid pGAR117 is a plant expression vector with a luxAB gene, a cauliflower mosaic virus 35S promoter and an octopine synthase termination sequence, particularly useful as a reporter gene system in plant cells, such as *Nicotiana plubmaginifolia* cells.

Plasmid pIT20 was used as a source of a luxAB gene in the construction of plasmid vector pSV2lux as described in Example 5. This plasmid vector drives expression of a luxAB gene product in animal cells. Plasmid pSV2lux was constructed by ligating an ~2.4 kb HindIII-XhoII fragment from plasmid pIT20 with HindIII-BglII cleaved and phosphated plasmid pSV2HNXB DNA. A restriction site and function map of plasmid pSV2lux is presented in FIG. 11 of the accompanying drawings. Plasmid pSV2lux is an animal cell expression vector with a luxAB gene and SV40 promoter, particularly useful as a reporter gene system in animal cells, such as COS-1 cells.

Plasmid pIT20 was used as a source of a luxAB gene in the construction of plasmid vector pIT22 as described in Example 6. This plasmid vector drives expression of a luxAB gene product in fungal cells. Plasmid pIT22 was constructed by ligating the following fragments: (1) an ~650 bp XmaI-HindIII restriction fragment from plasmid pIT30 that contains the *Cephalosporium acremonium* isopenicillin N synthase (IPNS) promoter sequence; (2) an ~2.4 kb HindIII-XhoII fragment from plasmid pIT20 which contains the luxAB gene; and (3) an ~6.1 kb XmaI-BglII fragment from plasmid pIT2 containing the sequences required for maintenance and selection in *E. coli* and *C. acremonium*. A restriction site and function map of plasmid pIT22 is presented in FIG. 16 of the accompanying drawings. Plasmid pIT22 is a fungal expression vector with a luxAB gene and an IPNS promoter, particularly useful as a reporter gene system in fungal cells, such as *C. acremonium* cells.

The expression vectors of the present invention provide a simple and efficient reporter gene system, which can be used to assay any transcriptional and/or translational activating sequence, such as a promoter, in bacterial, yeast, plant, animal, and fungal cells. The present invention also provides the starting material for the preparation of mutant luxAB fusion genes with increased luciferase enzyme activity. *E. coli* is the best host for mutational cloning experiments, and the *E. coli* expression vectors of the present invention can be readily mutated by procedures well known in the art, such as, for example, treatment with radiation (X-ray or UV) or chemical mutagens (such as ethylmethanesulfonate, nitrosoguanidine, or methyl metanesulfonate) or site-directed mutagenesis, to obtain mutant fusion proteins with increased luciferase activity.

The present invention is not limited to the particular vectors exemplified herein. Instead, the present invention also comprehends vectors which comprise fusion genes which encode α- and β-subunits with luciferase enzyme activity. The fusion genes of the present invention can be used to construct expression vectors which drive expression of a single polypeptide having luciferase enzyme activity, in any host cell in which the expression vector replicates or integrates, and in which the transcriptional and translational-activating sequence used to express the fusion gene encoding luciferase activity functions. Thus, the present invention comprises expression vectors which drive expression of a luxAB fusion gene and utilize a replicon functional in a host cell transformed or transferred with the expression vector.

The present invention is not limited to a particular transcriptional and translational activating sequence to drive expression of the luciferase activity encoding DNA. The present invention comprises the use of any transcriptional and translational activating sequence which is functional in a host cell and is used to express a luxAB fused gene product with luciferase activity. Many transcriptional and translational activating sequences functional in a wide variety of bacterial, yeast, plant, animal, and fungal cells, are known are suitable for driving expression of a luxAB fused gene product with luciferase activity. For example, in $E.$ $coli$ such transcriptional and translational activating sequences include, but are not limited to, the lpp, lac, trp, tac, $\lambda p_L$, and $\lambda p_R$ transcriptional and translational activating sequences.

In addition to the various $E.$ $coli$ transcriptional and translational activating sequences exemplified above, transcriptional and translational activating sequences from other organisms can be ligated to the present fusion reporter genes to form expression vectors which drive expression of luciferase activity in host cells in which the activating sequence functions, making a fusion reporter gene of the present invention particularly useful as a reporter gene system in a wide variety of bacterial, yeast, plant, animal and fungal cells.

The following Examples are provided to further illustrate and exemplify the present invention but are in no way intended to limit the scope of the present invention.

EXAMPLE 1

Isolation of Plasmid pIT20 and Use in $E.$ $coli$

A. Culture of $E.$ $coli$ K12 JA221/pIT20 and Isolation of Plasmid pIT20 DNA

A lyophil of $E.$ $coli$ K12 JA221/pIT20 is obtained from the Northern Regional Research Laboratory, 1815 North University Street, Peoria, Ill. 61604 (NRRL), under the Accession Number NRRl B-18301. The lyophil can be directly used as the "culture" in the process described below.

One liter of TY broth (10 g/l tryptone, 10 g/l NaCl, and 5 g/l yeast extract) containing 100 μg/ml ampicillin was inoculated with a culture of $E.$ $coli$ K12 JA221/pIT20 and incubated with aeration of 37° C. overnight (15–18 hours).

To isolate pIT20 plasmid DNA, the overnight culture was centrifuged in a Beckman JS-5.2 rotor (Beckman Instruments, Inc., Spinco Divsion, Palo Alto, Calif. 94304) at 5200 rpm for 25 minutes at 4° C. The resulting supernatant was discarded. The cell pellet was resuspended in 28 ml of a solution of 25% sucrose and 50 mM EDTA. About 1 ml of a solution of 20 mg/ml lysozyme in 50 % glycerol and 0.25 M Tris-HCl, pH=8.0, and about 1.5 μl of 0.5 M EDTA, pH=8.0, were added to and mixed with the cell suspension. The resulting mixture was incubated on ice for 15 minutes. Three ml of lysing solution (prepared by mixing 3 ml of 10% Triton-X100; 75 μl of 0.25 M EDTA; pH=8.0; and 7 ml of H$_2$O) were added to the lysozyme-treated cells with gentle mixing. The resulting solution was incubated on ice for another 15 minutes.

The cellular debris was removed from the solution by centrifugation at 17,000 rpm in a Beckman JA-17 rotor for about 45 minutes at 4′ C. About 28.6 g of cesium chloride (CsCl) and ~1 ml of a 5 mg/ml ethidium bromide solution were added to the ~30 ml of supernatant. Then, the volume was adjusted to 40 ml with H$_2$O and the solution decanted into a VTi50 ultracentrifuge tube (Beckman). The tube was sealed, and the solution was centrifuged in a VTi50 rotor at 49,500 rpm for ~18 hours. The resulting plasmid band, visualized with ultraviolet light, was isolated, extracted with salt-saturated isopropanol to remove the ethidium bromide, and dialysed against three changes of ~°volumes of TE buffer (10 mM Tris-HCl, pH=7.5; 1 mM EDTA). The dialysate was collected; then, two volumes of ethanol and 0.05 volumes of 3 M sodium acetate (NaOAc) solution were added. The ethanol mixture was cooled to ~20° C., and the plasmid DNA was pelleted by centrifugation in a JA-17 rotor (Beckman) at 10,000 rpm for 30 minutes at $-10°$ C. The resulting pellet was resuspended in ~1 ml of TE buffer and then extracted with an equal volume of a phenol-chloroform mixture (1:1, v/v). The DNA in the aqueous phase was recovered by the addition of 0.1 volume of 3 M NaOAc and 2 volumes of ethanol, followed by incubation at $-20°$ C. for ~30 minutes and centrifugation at 15,000 rpm for 20 minutes. The resulting DNA pellet was rinsed first with 70% ethanol and then with 100% ethanol and dried.

The ~1.5 mg of plasmid pIT20 DNA obtained by this procedure is suspended in 1.5 ml of 0.1×TE buffer (1×TE buffer=10 mM Tris-HCl, pH=7.5; 1 mM EDTA, pH=8.0) and stored at $-20°$ C. A restriction site and function map of plasmid pIT20 is presented in FIG. 1 of the accompanying drawings.

B. Measurement of luciferase activity in $E.$ $coli$ K12 JA221/pIT20 cells $E.$ $coli$ K12 JA221/pIT20 cells were grown in substantial accordance with the procedure of Example 1A. Ten μl of undiluted decanal (decyl aldehyde, Sigma) were added to 1 ml of the culture in a glass scintillation vial and counted immediately. The photons produced were measured in a Beckman LS7000 scintillation counter using 0.1 minute counts and an open $^{32}P$ channel.

EXAMPLE 2

Construction and Use of Plasmid pIT24

A. Isolation of Plasmid pIT217 DNA

Plasmid pIT217 has been disclosed previously in U.S. patent application Ser. No. 07/208,793, filed Jun. 17, 1988, incorporated herein by reference. Briefly, pIT217 contains a portion of the yeast 2 micron plasmid and the yeast URA3 gene (for maintenance and selection in appropriate yeast host cells), the origin of replication and ampicillin resistance gene from plasmid pBR322 (for maintenance and selection in $E.$ $coli$ host cells), and the yeast YG100 heat shock promoter fused in a protein coding region fusion to a bacterial hygromycin B resistance gene. $E.$ $coli$ K12 JA221/pIT217 cells were grown and pIT217 DNA isolated in substantial accordance with the procedure of Example 1A.

B. Digestion of Plasmid pIT217 DNA

Twenty μg of plasmid pIT217 DNA were added to 20 82 1 of 10×BamHI buffer (10×BamHI buffer=0.5 M NaCl, 0.5 M Tris-HCl, pH=8.0, 0.1 M MgCl$_2$) and H$_2$O was added to reach a total volume of 190 μl. Ten μl (50 units) of BamHI restriction enzyme were added, the solution was gently mixed, and incubation was carried out at 37° C. for 90 minutes. The resulting BamHI-digested DNA is extracted with an equal volume of a 1:1 mixture of phenol:chloroform (CHCl$_3$), then extracted with an equal volume of CHCl$_3$ (or with CHCl$_3$:isoamyl alcohol), and finally ethanol precipitated by addition of 3 M NaOAc to reach a final concentration of 0.2 M and addition of 2 volumes of cold 95% ethanol. The mixture is vortexed and incubated on ice for 10 minutes, then centrifuged at 4° C. at approximately 13,000×g for 10 minutes (or microfuged for 30 minutes). The resulting pellet is rinsed with cold 95% ethanol (or 70% ethanol), dried under a vacuum, and resuspended in 10 μl 0.1×TE.

C. Klenow Treatment of BamHI digested Plasmid pIT217 DNA

The resulting DNA solution from Example 2B was then treated with *E. coli* DNA polymerase I-large fragment (Klenow enzyme). First, 2.5 μl of 10×Klenow buffer (10×Klenow buffer=0.5 M Tris-HCl, pH=7.5; 0.1 M MgCl$_2$), 2.5 μl of a solution containing 0.3 mM each of dGTP, dATP, dCTP and TTP and 8 μl of H$_2$O were added to the DNA. Then 2 μl (approximately 5 units) of Klenow enzyme were added, the solution was gently mixed, and the mixture was incubated at 37° C. for 15 minutes. The DNA was then purified in substantial accordance with the procedure of Example 2B.

D. Digestion of BamHI-Klenow Treated Plasmid pIT217 DNA

The BamHI-digested, Klenow-treated plasmid pIT217 DNA was digested with restriction enzyme BglII as described in Example 2B except that BglII restriction enzyme was substituted for BamHI restriction enzyme. The resulting digestion mixture was purified in substantial accordance with the procedure of Example 2B.

E. Digestion of Plasmid pIT20 with HindIII and Klenow treatment

Twenty μg of plasmid pIT20 DNA, isolated as described in Example 1A, was digested with restriction enzyme HindIII in substantial accordance with the procedure of Example 2B except that restriction enzyme HindIII was substituted for BamHI. The DNA was then purified in substantial accordance with the procedure of Example 2B, treated with Klenow enzyme in substantial accordance with the procedure of Example 2C, and purified again.

F. Digestion of HindIII-cleaved, Klenow-treated Plasmid pIT20 DNA with XhoII and Isolation of an Approximately 2.4 kb Fragment The HindIII-cleaved, Klenow-treated plasmid pIT20 DNA was then cleaved with XhoII, which cleaves at the BamHI-BglII junction downstream of the luxAB fusion which was created during the construction of plasmid pIT20. the XhoII cleavage was carried out in substantial accordance with the procedure of Example 2B except that XhoII restriction enzyme was substituted for BamHI. The desired ~2.4 kb fragment was then purified away from the ~2.7 kb vector backbone. The isolation and purification of the ~2.4 kb fragment was accomplished by agarose gel electrophoresis and other conventional fragment isolation procedures (Maniatis et al., 1982, *Molecular Cloning—A Laboratory Manual*, Cold Spring Harbor Laboratory, Cold Spring Harbor, N.Y.). The resulting ~5 μg of DNA was resuspended in 10 μl DNA and constitutes the desired ~2.4 kb HindIII Klenow-treated-XhoII fragment.

G. Construction of Plasmid pIT24

1 μl (~10 ng) of the BamHI Klenow-treated-BglII digested plasmid pIT217 DNA prepared as described above in Example 2B-2D and 1 μl (~125 ng) of the ~2.4 kb HindIII Klenow-treated-XhoII fragment isolated from plasmid pIT20 DNA as described above in Example 2E and 2F are added to 1 μl of 10×ligase buffer (10×ligase buffer=0.5 M Tris-HCl, pH=7.8; 0.1 M MgCl$_2$; 0.2 M dithiothreitol (DTT), 1 μl 10 mM ATP and 4 μl H$_2$O. After 1-2 μl (~500-1000 units) of T4 DNA ligase (New England Biolabs) and 1 μl (~0.4 units) of T4 RNA ligase (New England Biolabs), are added to the mixture of DNA, the resulting reaction is incubated at 16° C. overnight.

*E. coli* K12 JA221 cells are available in lyophilized form from the Northern Regional Research Laboratory under the accession number NRRL B-15211. *E. coli* K12 JA221 cells are cultured, made component for transformation, and transformed with the ligated DNA prepared above as follows. A 50 ml culture of *E. coli* K12 JA221 in TY broth is grown to an optical density at 650 nanometers (O.D.$_{650}$) of approximately 0.4 absorbance units. The culture is chilled on ice for ten minutes, and the cells are collected by centrifugation. The cell pellet is resuspended in 25 ml of cold 100 mM MgCl$_2$ and incubated on ice for 25 minutes. The cells are once again pelleted by centrifugation, and the pellet is resuspended in 2.5 ml of cold 100 mM CaCl$_2$ and incubated for 30 minutes on ice. After the incubation, the cells are competent for the uptake of transforming DNA.

Two hundred μl of this cell suspension are mixed with the ligated DNA prepared above and incubated on ice for 30 minutes. At the end of this period, the cells are placed in a H$_2$O bath at 42° C. for 2 minutes and then returned to the ice for an additional 10 minutes. The cells are collected by centrifugation and resuspended in 1 ml of TY broth and incubated at 37° C. for 1 hour. Aliquots of the cell mixture are plated on TY-agar plates containing 100 μg/ml ampicillin. The plates are incubated at 37° C. overnight. *E. coli* JA221/pIT24 transformants were identified by their ampicillin-resistant phenotype and by restriction enzyme analysis of their plasmid DNA. Plasmid DNA was obtained from the *E. coli* K12 JA221/pIT24 cells in substantial accordance with the procedure of Example 1A. A restriction site and function map of plasmid pIT24 is presented in FIG. 2 of the accompanying drawings.

EXAMPLE 3

Construction and Use of Plasmid pIT21

A. Construction of Plasmid pIT140

Plasmid pKC7 is available from the American Type Culture Collection (ATCC), 1230 Parklawn Drive, Rockville, Md. 20852 under Accession Number 37084. Plasmid YEp24 is available from ATCC under Accession Number 37051. Plasmid DNA of both types were prepared in substantial accordance with the procedure of Example 1A. Approximately 2 μg of the ~1.1 kb HindIII fragment from YEp24 which contains the yeast URA3 gene were isolated and purified in substantial accordance with the procedure of Example 2B and 2F except that YEp24 DNA and restriction enzyme HindIII were used.

Plasmid pKC7 was cleaved with restriction enzymes HindIII in substantial accordance with the procedure of Example 2B except that pKC7 DNA and restriction enzyme HindIII were used. The DNA was purified as described in Example 2B.

Figure 3:
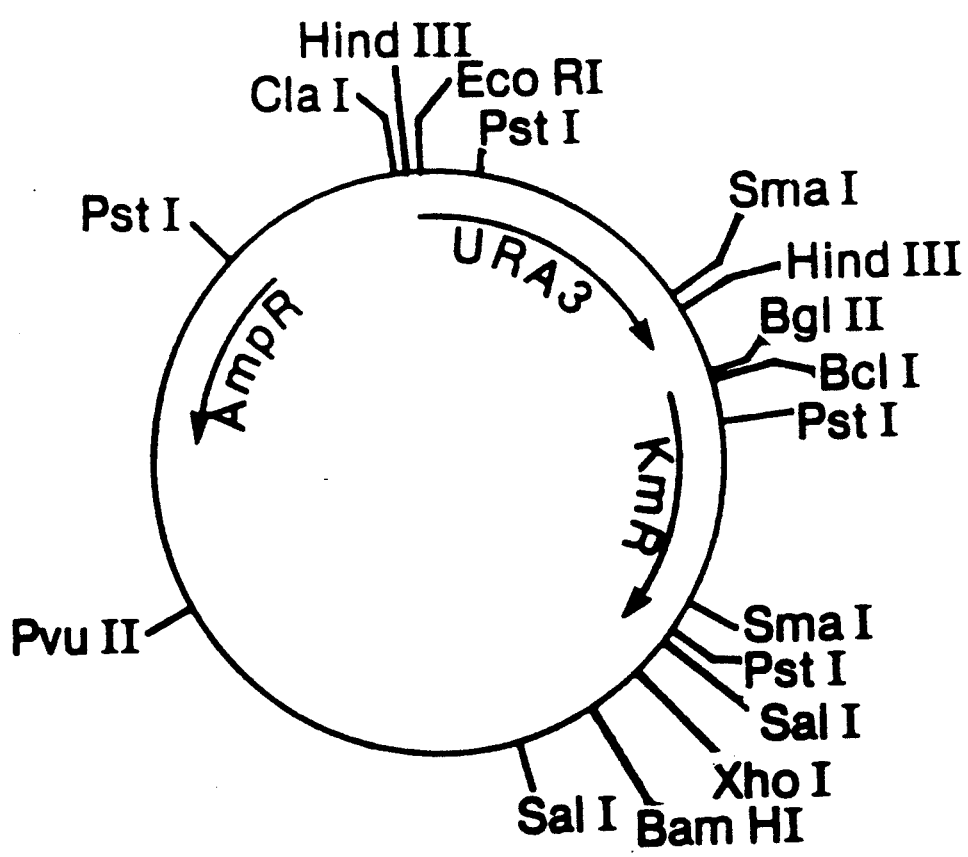
FIG. 3 shows the restriction site and function map of plasmid pIT140.

Approximately 1 μg each of the ~1.1 kb HindIII fragment from YEp24 and HindIII-cleaved pKC7 were mixed and ligated in substantial accordance with the procedure of Example 2G. The ligation mix was transformed into E. coli K12 JA221 and the desired isolate pIT140 was identified in substantial accordance with the procedure of Example 2G. Plasmid pIT140 DNA was prepared in substantial accordance with the procedure of Example 1A. A restriction site and function map of plasmid pIT140 is shown in FIG. 3. The orientation shown is designated pIT140A.

B. Construction of Plasmid pIT214

The ~2.24 kb EcoRI fragment of plasmid YEp24 which contains replicative functions from the yeast 2 micron plasmid was isolated and purified in substantial accordance with the procedure of Example 2B and 2F except that YEp24 DNA, 10×EcoRI buffer (10×EcoRI buffer=1 M Tris-HCl, pH=7.5, 0.1 M MgCl$_2$, 0.5 M NaCl), and restriction enzyme EcoRI were used.

Plasmid pIT140 DNA, preparation of which was described in Example 3A, was cleaved with EcoRI and purified in substantial accordance with the procedures of Examples 2B and 2F except that pIT140 DNA, 10×EcoRI buffer and restriction enzyme EcoRI were used.

Figure 4:
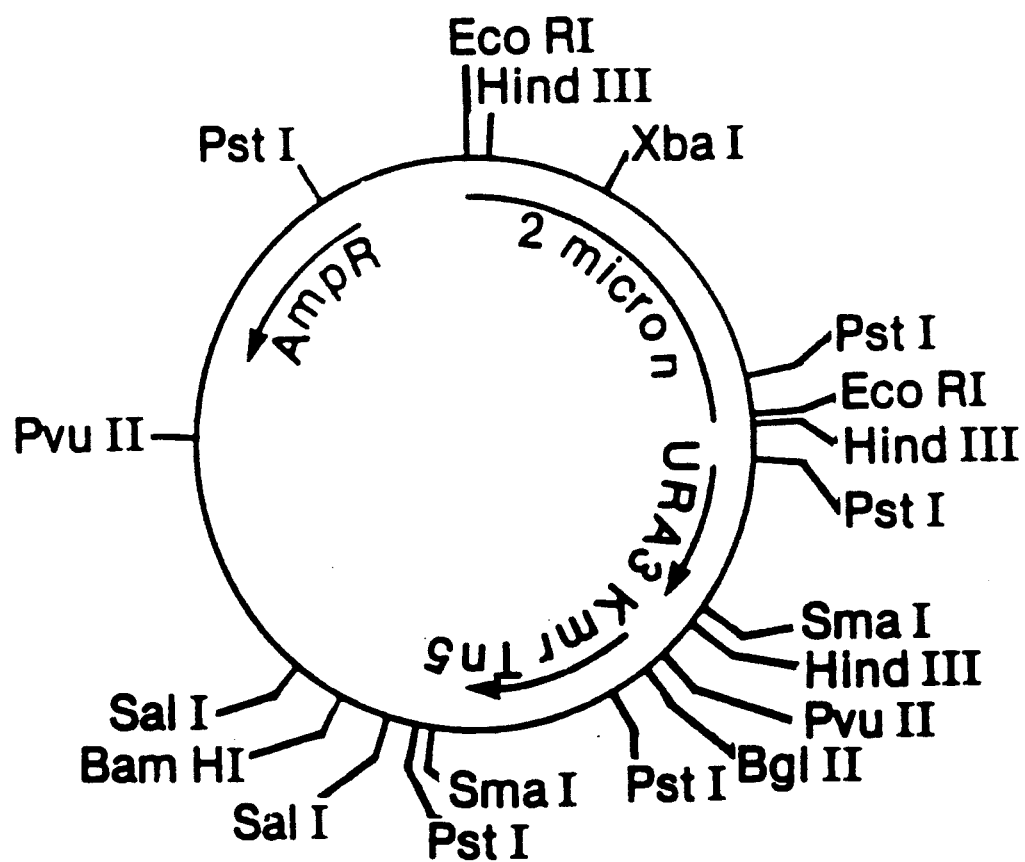
FIG. 4 shows the restriction site and function map of plasmid pIT214.
Figure 5:
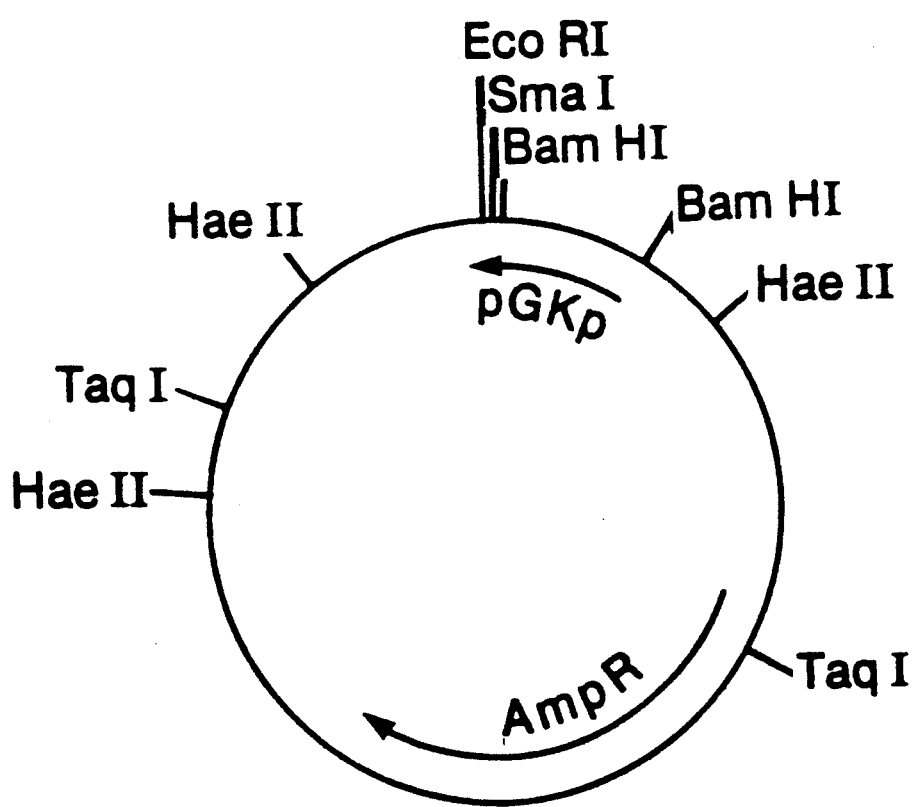
FIG. 5 shows the restriction site and function map of plasmid pIT143.

The ~2.24 kb EcoRI fragment from YEp24 and the EcoRI-cleaved pIT140 DNA were mixed and ligated, and the ligation mixture was transformed into E. coli K12 JA221 cells, all in substantial accordance with the procedure of Example 2G. Both orientations of the desired recombination were obtained from among the transformants. Plasmid DNA from one of the orientations, designated pIT214A, was prepared in substantial accordance with the procedure of Example 1A. A restriction site and function map of plasmid pIT214 is shown in FIG. 4.

C. Construction of Plasmid pIT143

Plasmid pIT141 contains the entire phosphoglycerate kinase (PGK) gene and was used as a source of the yeast PGK gene promoter to construct plasmid pIT143. Plasmid pIT141 can be obtained from NRRL under Accession Number B-15602, and pIT141 DNA is prepared in substantial accordance with the procedure of Example 1A. The construction of plasmid pIT143 is taught in U.S. patent application Ser. No. 07/208,793, filed Jun. 17, 1988, and U.S. Pat. No. 4,762,786, both hereby incorporated by reference. Briefly, plasmid pIT143 is constructed by digesting the ~958 bp ClaI-HincII fragment of plasmid pIT141 with the restriction enzyme MboII, removing the resultant extensions with Klenow enzyme, attaching BamHI linkers with the sequence TGGATCCA and then ligating the linker-containing fragment into BamHI-digested plasmid pUC8 DNA.

D. Construction of Plasmid pIT222

The yeast PGK gene promoter was isolated from plasmid pIT143 on an ~180 bp SauIIIA fragment. First, pIT143 was digested with BamHI in substantial accordance with the procedure of Example 2B, except that plasmid pIT143 DNA and restriction enzyme BamHI were used. The desired ~260 bp BamHI fragment was isolated and purified from acrylamide using conventional methods (Schlief and Wensick, 1981, *Practical Methods in Molecular Biology*, Springer-Verlag, New York; Maniatis et al., supra). This fragment was then further cleaved with restriction enzyme SauIIIA. The ~1.5 μg of the ~260 bp BamHI fragment was suspended in a total volume of 40 μl of H$_2$O. Five μl of 10×SauIIIA buffer (10×SauIIIA buffer=0.5 M NaCl; 0.06 M Tris-HCl, pH=7.5; 0.06 M MgCl$_2$; 0.6 M beta-mercaptoethanol) were added, followed by 5 μl (10 units) of restriction enzyme SauIIIA. After 90 minutes incubation at 37° C., the desired ~180 bp BamHI-SauIIIA fragment was isolated and purified as described above.

Plasmid pIT214A DNA, prepared as described in Example 3B, was digested with BamHI and BglII in substantial accordance with the procedure of Example 2B. Twenty μg of pIT214 DNA was suspended in a total volume of 170 μl of H$_2$O. Twenty μl of 10×BamHI buffer was added, followed by 5 μl each (25 units each) of BamHI and BglII. After 90 minutes of incubation at 37° C., the DNA was purified as described in Example 2B.

Figure 6:
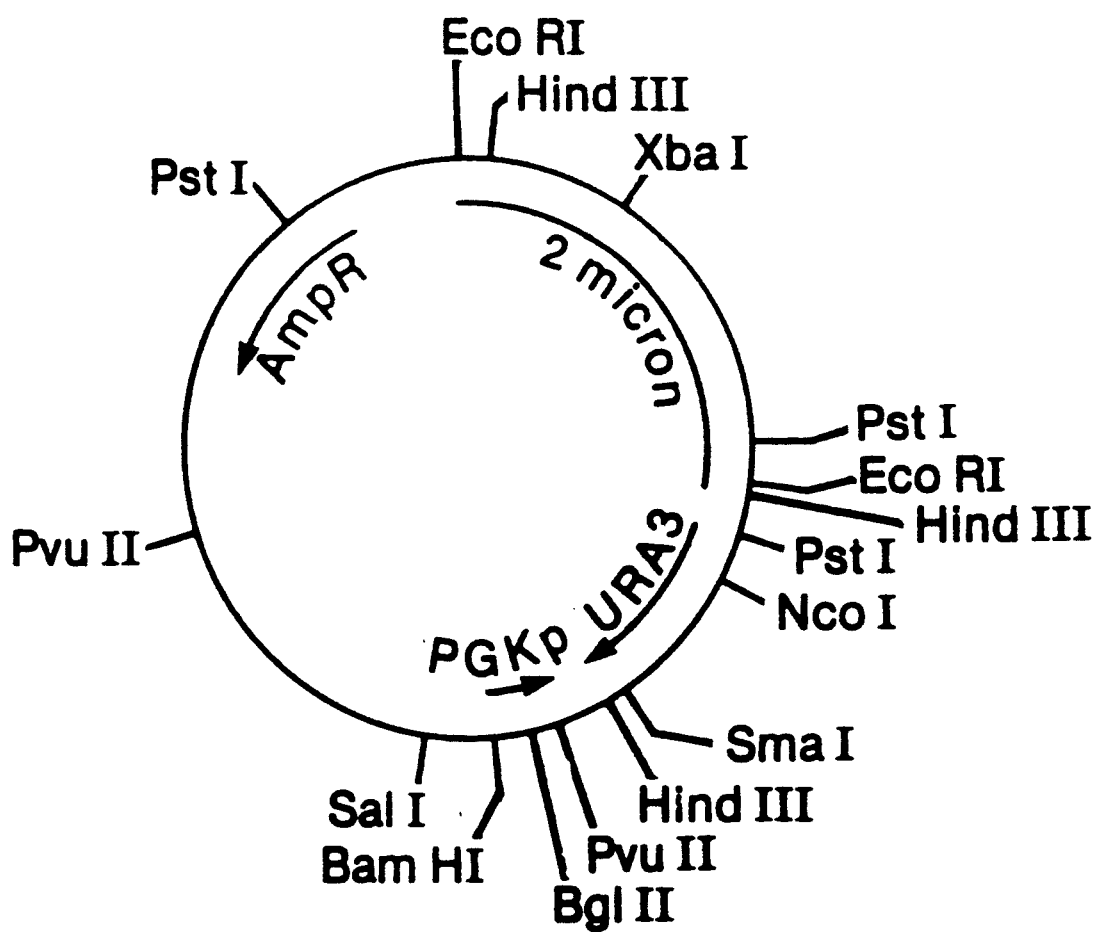
FIG. 6 shows the restriction site and function map of plasmid pIT222.

Approximately, 1 μg of the ~180 bp BamHI-SauIIIA fragment was then ligated with ~1 μg of the BamHI- and BglII-digested pIT214A DNA in substantial accordance with the procedure of Example 2G. The ligation mixture was transformed into E. coli K12 JA221 cells, and the transformants analyzed in substantial accordance with the procedure of Example 2G. The desired isolate with the ~180 bp BamHI-SauIIIA fragment in the orientation which recreates the BamHI and BglII sites (since the SauIIIA site used in pIT143 is preceded by an A residue, it will reconstruct the BglII site) was identified and designated pIT222. DNA was prepared in substantial accordance with the procedure of Example 1A. A restriction site and function map of plasmid pIT222 is shown in FIG. 6.

E. Digestion of Plasmid pIT222

Approximately 50 μg of plasmid pIT222 DNA, prepared as described in Example 3D, was suspended in a total volume of 350 μl H$_2$O. Forty μl of 10×SmaI buffer (10×SmaI buffer=0.2 M KCl; 0.06 M Tris-HCl, pH=8.0; 0.06 M MgCl$_2$; 0.06 M beta-mercaptoethanol; 1 mg/ml bovine serum albumin (BSA)) and 10 μl (100 units) of SmaI restriction enzyme were added to the DNA. The mixture was incubated at 25° C. for 2 hours, then the DNA was purified in substantial accordance with the procedure of Example 2B. The SmaI-digested DNA was resuspended in 85 μl of H$_2$O, 10 μl of 10×BamHI buffer were added, and 5 μl (25 units) of restriction enzyme BglII were added. The mixture was incubated at 37° C. for ~2 hours, after which the DNA was electrophoresed on a 0.8% agarose gel and the desired ~7.5 kb fragment was isolated and purified in substantial accordance with the procedure of Example 2F. The ~20 μg of DNA was resuspended in ~20 μl of H$_2$O.

F. Isolation of the LuxAB Gene

The luxAB gene was isolated on two fragments from plasmid pIT20. In one reaction, 50 82 g of pIT20 DNA prepared as described in (Example 1) were digested with HindIII restriction enzymes and XbaI as follows. The DNA was suspended in 160 μl of H₂O, and 20 μl of 10×BamHI buffer were added. Ten μl each (50 units each) of restriction enzyme HindIII and XbaI were added and the mixture was incubated at 37° C. for 2 hours. The resulting digest was electrophoresed on a 7% acrylamide gel and the desired ~1.1 kb HindIII-XbaI fragment was isolated and purified in substantial accordance with the procedure of Examples 2F and 3D. The fragment was redissolved in 30 μl of distilled H₂O.

In a parallel digestion, pIT20 DNA was digested with restriction enzymes PvuII and XbaI as described above except restriction enzyme PvuII was used instead of HindIII. The desired ~1.3 kb XbaI-PvuII fragment was isolated and purified as described above for the ~1.1 kb HindIII-XbaI fragment. The ~1.3 kb XbaI-PvuII fragment was dissolved in 30 μl of H₂O.

G. Adaptor Linkers to Join the HindIII and BamHI Sites

Commercial adaptor linkers were purchased from New England BioLabs (32 Tozer Road, Beverly, Mass. 01915). Equal amounts of 5' HindIII-XmnI adaptors (AGCTCGAAGGGGTTCG) (NEB#1107) and 5' BamHI-XmnI adaptors (GATCCGAACCCCTTCG) (NEB#1108) were kinased and annealed according to the manufacturers instructions. Linkers may also be synthesized in substantial accordance with the procedures of Example 5B.

H. Construction of Plasmid pIT21

Four μl (~1 μg) of the ~1.1 kb HindIII-XbaI fragment (Example 3F), 4 μl (~1 μg) of the ~1.3 kb XbaI-PvuII fragment (Example 3F), 2 μl (~1 μg) of the SmaI-BglII cleaved pIT222 (Example 3E) and 2 μl (~10 pmoles) of the annealed adaptor linker (Example 3G) were mixed and ligated at 16° C. overnight. The ligation mixture was then used to directly transform yeast DBY746 cells.

The desired transformation of yeast DBY746 cells was carried out using yeast protoplasts in substantial accordance with the teaching of Hinnen et al., 1978, Proc. Natl. Acad. Sci. USA 75:1929 with minor modifications. Assuming sterile conditions and a culture volume of 100 ml, *Saccharomyces cerevisiae* DBY746 (ATCC 44773 and also available from the Yeast Genetic Stock Center, Berkeley, Calif. 94720) was first grown in YPD (1% Bacto-Yeast Extract, 2% Bacto-Peptone, 2% Glucose) to an O.D.$_{600}$ of about 1.0 and then washed in 15 ml of 1.2 M sorbitol. After suspension in another 15 ml of volume of 1.2 M sorbitol, about 100 μl of 2.5 mg/ml zymolase 60,000 (prepared by suspending the zymolase in 5 mM potassium phosphate; pH=7.6 and 1.2 M sorbitol) were added. The suspension was incubated at room temperature and the extent of protoplasting monitored by suspending 20 μl aliquots in 180 μl of 10% SDS and observing under a phase contrast microscope. Protoplasts appear black under phase contrast in SDS solution. When protoplasting was about 90% complete, the protoplasts were washed twice in 15 ml of 1.2 M sorbitol, collected by centrifugation with as little g force as possible and resuspended gently in 600 μl of YPD containing 1.2 M sorbitol, 10 mM calcium chloride and 10 mM Tris-HCl, pH=7.5.

Transformation was carried out by adding about 20 μl of the ligation mixture to 0.2 ml aliquots of the protoplast suspension. The resultant mixture was incubated at room temperature for 10 minutes and then, after addition of 1 ml of 20% PEG 3350 (polyethyleneglycol), 10 mM calcium chloride and 10 mM Tris-HCl, pH=7.5, incubated again for 60 minutes. Different volumes of the transformed protoplasts were plated in 25 ml of 3% regeneration agar containing required nutrients. Regeneration agar was prepared with the following composition: 0.67% yeast nitrogen base without amino acids (obtained from Difco); 3% agar; 1.2 M sorbitol; conventional required nutrients (except for marker on plasmid). The agar was stored in a H₂O bath at 45° to 50° C. before plating and, after solidification, the plates were incubated at 30° C. for 48 to 72 hours.

Figure 7:
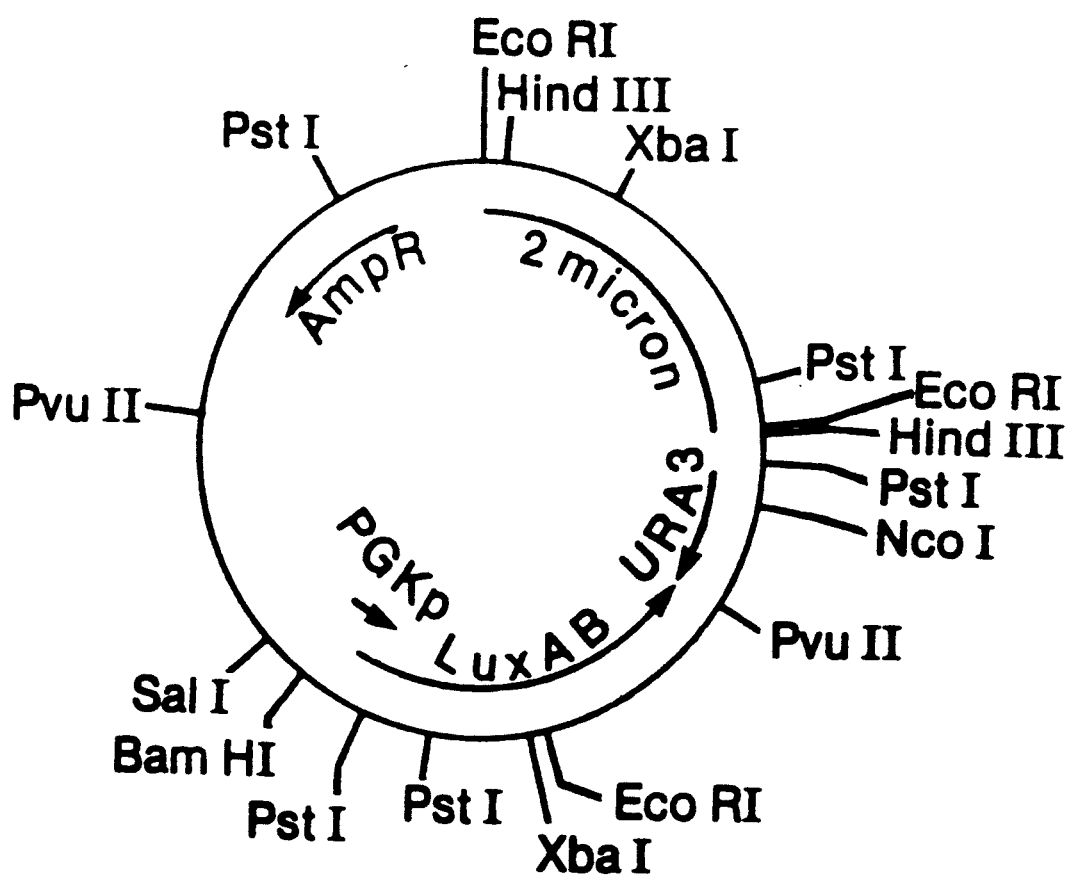
FIG. 7 shows the restriction site and function map of plasmid pIT21.

The yeast transformants were screened for their ability to produce light in the presence of decyl aldehyde as described in Example 1B. Transformants were grown and plasmid DNA was isolated from these transformants as follows. The cells are grown to stationary phase (for 16 hours, at 30° C.) in a medium containing 0.67% yeast nitrogen base without amino acids (Difco) and conventional required nutrients (except for marker on plasmid). Cells are pelleted from ~30 ml of cell culture by centrifugation. The cell pellet is washed with ~4 ml of 50 mM Tris-HCl, pH=7.5, 50 mM NaCl, and 10 mM EDTA. The cells are resuspended in ~500 μl of 20 mM Tris-HCl, pH=7.5, 150 mM NaCl, and 10 mM EDTA. Then, ~50 μl of 100 mM DTT, and 10 μl of 10 mg/ml zymolase 5,000 (the zymolase may be stored in the following solution: 20 mM Tris-HCl, pH=7.5, 150 mM NaCl, 10 mM DTT and 40% glycerol) are added and the cell suspension is incubated at 37° C. for 30 minutes. After this incubation, ~50 μl of 0.5 M EDTA and ~5 μl of 10% Triton-X100 are added. After incubation at room temperature for 15 minutes, the cell suspension is centrifuged for 15 minutes in an Eppendorf, and the pellet is discarded. The DNA is extracted with phenol:CHCl₃ twice and precipitated with ethanol. Approximately 1.5 μg of yeast plasmid DNA is recovered. The desired construction was obtained and designated plasmid pIT21, a restriction site and function map of which is shown in FIG. 7.

EXAMPLE 4

Construction of pGAR117 and Its Use in Plant Cells

A. Preparation of Plasmid pGAR88

Figure 8:
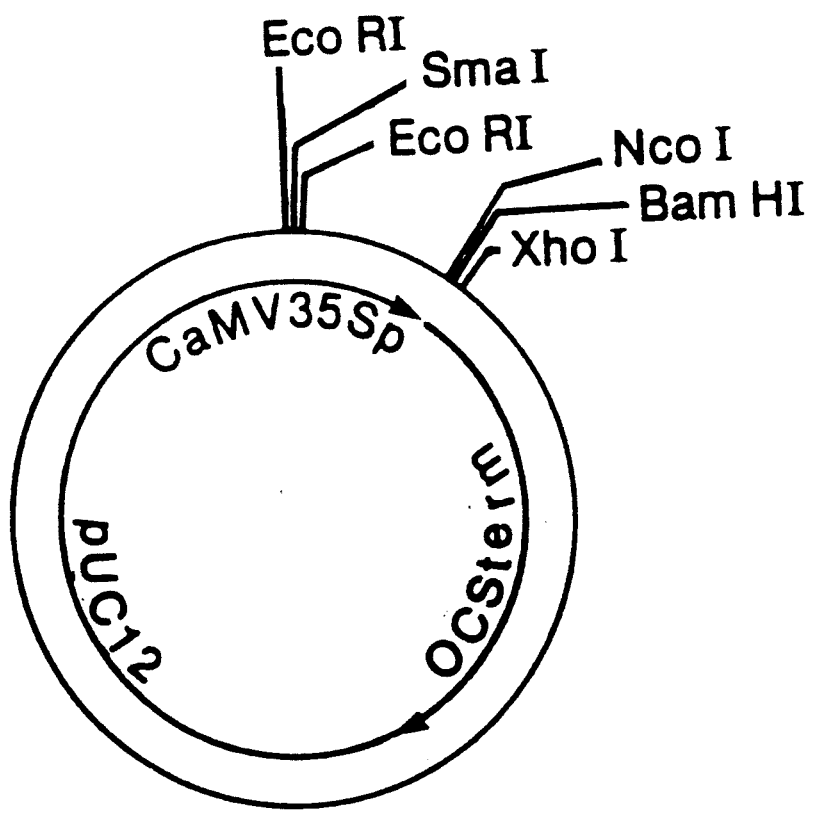
FIG. 8 shows the restriction site and function map of plasmid pGAR88.

The luxAB gene of the present invention was inserted between the cauliflower mosaic virus 35S promoter and the octopine synthase termination sequence to facilitate expression in plant cells. The genetic elements for plant expression are contained in pGAR88; a restriction site and function map of pGAR88 is shown in FIG. 8. Plasmid pGAR88 has been deposited at the NRRL and is available under Accession Number B-18302. Plasmid pGAR88 DNA is prepared in substantial accordance with the procedure of Example 1A.

B. Cleavage, Klenow and Phosphatase Treatment of Plasmid pGAR88

Plasmid pGAR88 contains a translational start site and an XhoI site downstream of the transcription initiation site of the cauliflower mosaic virus 35S promoter.

The translational start site is nested in an NcoI restriction site. The sequence in question is:

5'-CCATGGGATCCAGCTCGAG-3'

Plasmid pGAR88 was cleaved with XhoI in substantial accordance with the procedure of Example 2B except that ~3 μg of pGAR88 DNA, 5 μl of 10×BamHI buffer and 10 units of the restriction enzyme XhoI were used in a final volume of 50 μl. The resulting XhoI-digested DNA was purified in substantial accordance with the procedure of Example 2B except that after the addition of 95% ethanol, the mixture was incubated at −70° C. for 60 minutes and then microfuged for 10 minutes to pellet the DNA.

The XhoI-cleaved pGAR88 DNA was then treated with Klenow enzyme in substantial accordance with the procedure of Example 2C and purified as described above. The resulting DNA, constituting ~3.0 μg of the desired XhoI-cleaved, Klenow-treated pGAR88 DNA, was resuspended in 42 μl H₂O. Five μl of 10×calf intestinal alkaline phosphatase (CIAP) buffer (10×CIAP buffer=500 mM Tris-HCl, pH=8.0) and 3 μl (1.5 units) of CIAP were added to the DNA and the mixture was incubated at 37° C. for 60 minutes. The Klenow-treated dephosphorylated DNA was purified essentially as described above and resuspended in 50 μl H₂O.

C. Isolation of the LuxAB Gene

The luxAB gene was isolated from plasmid pIT20 on a ~2.25 kb fragment with blunt ends. Plasmid pIT20 was digested with HindIII and treated with Klenow enzyme in substantial accordance with the procedure of Example 2E and purified in substantial accordance with the procedure of Example 4B. The DNA (~3.0 μg) was then cleaved with restriction enzyme PvuII, which cleaves downstream of the translational stop of the LuxAB gene. The PvuII digestion was carried out in substantial accordance with the procedure of Example 4B except that pIT20 DNA and the restriction enzyme PvuII were used. The DNA was purified in substantial accordance with the procedure of Example 4B and resuspended in 50 μl of H₂O.

D. Construction of Plasmid pGAR117

Figure 9:
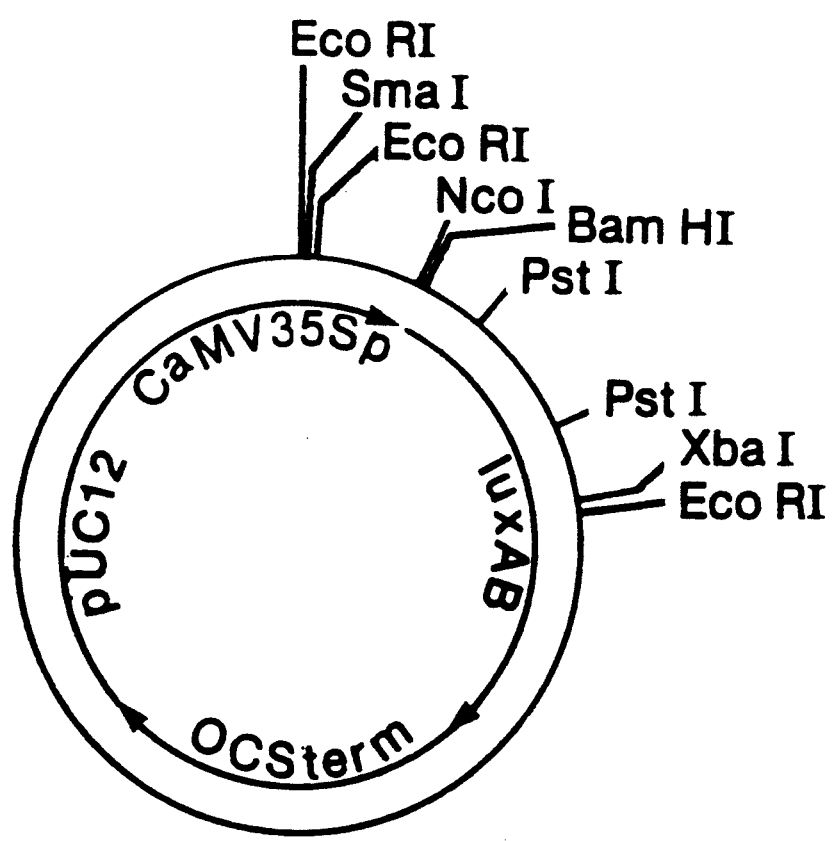
FIG. 9 shows the restriction site and function map of plasmid pGAR117.

Six μl (~0.35 μg) of the DNA containing the luxAB gene fragment described in Example 4C was mixed with 4 μl (~0.25 μg) of the XhoI-cleaved, Klenow and CIAP treated pGAR88 DNA described in Example 4B, and the fragments were ligated in substantial accordance with the procedure of Example 2G. The ligation mixture was transformed into E. coli K12 RR1ΔM15 cells and the desired orientation of the recombinant plasmid was identified among the ampicillin-resistant transformants by restriction enzyme analysis of their plasmid DNA. A restriction site and function map of the desired plasmid, designated pGAR117, is shown in FIG. 9. This construction encodes a methionine and six additional amino acids immediately upstream and in the same reading frame as the translation initiation codon of the luxAB gene. The sequence starting at the NcoI site from pGAR88 and ending with the translation initiation site of the natural LuxA gene, is 5'-CCATGGGATC-CAGCTCGAAGCTTATG. Plasmid pGAR177 DNA was prepared in substantial accordance with the procedure of Example 1A.

E. Transformation of Plant Cells with Plasmid pGAR117 DNA and Preparation of Cell Free Extracts Leaf protoplasts of sterilely grown Nicotiana plumbaginifolia were prepared and transformed as described by Waldron, et al., 1985, Plant Molec. Biol. Rep. 3:169–173. Four million viable protoplasts were transformed with pGAR117 and calf thymus (carrier) DNA in the proportions given by Waldron et al., 1985, supra. After three days' culture in the dark, the cells were collected by centrifugation and frozen at −20° C. On thawing they were mixed 1:1 with 2×plant grinding buffer (adapted from Koncz et al., 1987, Proc. Natl. Acad. Sci. USA 84:131–135; 1×plant grinding buffer=50 mM potassium phosphate pH=7.0; 5.5 mM beta-mercaptoethanol; 0.2% BSA). The cells were homogenized in a test tube with a small glass pestle and centrifuged in a microfuge (5 minutes × 12,000 rpm) and the supernatant collected. Luciferase activity was assayed in a scintillation counter in a protocol using a linked NADH:FMN reductase to extend the lifetime of the luciferase pulse for easier measurement, as described in Example 4F below. The results of this assay were as follows: an extract of 0.25 million cells gave activity comparable to that exhibited by 50 ng of Vibrio harveyi luciferase protein as obtained from Sigma Chemical (P.O. Box 14508, St. Louis, Mo. 63178) and assayed in the same reaction (each yielded about 4000 cpm in an unquenched tritium channel). An extract of untransformed cells gave no signal (80 cpm).

F. Assay of Light Emission from Plant Cells Containing Plasmid pGAR117 DNA

Cell free extracts prepared as described in Example 4E, were assayed for Lux gene product (bacterial luciferase) activity in the presence of an FMN-generation system. The following solutions were prepared and used in the assay reaction described below:

1. Assay Buffer: 50 mM potassium phosphate, pH=7.0 (prepare from 1 M stock and adjust pH to 7.0 on day of use), 0.55 mM beta-mercaptoethanol (BioRad) (0.035% v/v), and BSA 0.1% (w/v);
2. Enzyme Buffer: 5 ml of 1 M potassium phosphate buffer in about 40 ml distilled H₂O, adjust to pH=7.0, then and dissolve 37.2 mg Na₂EDTA and 1.5 mg dithiothreitol (DTT), then add 45 ml glycerol; then adjust to a volume of 100 ml and chill;
3. NADH Solution (Sigma grade III, 97%): make up as 20 mg/ml in chilled Assay Buffer just before use in assay;
4. FMN Solution (Sigma 80% sodium salt): make up as 6 mg/50 ml in Assay Buffer on day of use in assay, and store at room temperature in a foil covered bottle;
5. NAD(P)H:FMN Reductase Solution from Vibrio fischeri (Boehringer Mannheim Biochemicals, 7941 Castleway Drive, Indianapolis, Ind. 46250): prepare (per supplier's instructions) as 20 U (1 vial) per 1.0 ml Enzyme Buffer on ice (may be stored for several weeks at 4° C.);
6. Bacterial Luciferase Solution from Vibrio harveyi (Sigma): On the day of the assay, a 2 mg/ml solution of the lyophilized enzyme (equivalent to 1 mg/ml of protein) in Assay Buffer is diluted 1:100 with the Assay Buffer and used as a positive control.

Using the above described solutions, the luciferase enzyme assay was performed according to the following steps:

To 15 ml of room temperature Assay Buffer in a scintiallation vial are added:
1. 100 μl (2U) of the FMN Reductase Solution (swirl to dissolve);
2. 0.5 ml (0.1 μmoles) of the FMN solution (final concentration=6.25 μM);
3. 0.5 ml (1.4 μmoles) of the NADH solution (final concentration=85 μM);
4. 50 μl of undiluted decanal (decylaldehyde, Sigma) (swirl vigorously to distribute);
5. 1-1000 μl of the sample containing luciferase enzyme (e.g. Bacterial Luciferase Solution at plant cell-free extract prepared as in Example 4E).

With the addition of the sample containing luciferase enzyme (step 5above), the scintillation vial is capped quickly, shaken and placed in a scintillation counter. The vials are counted at short intervals (~6 seconds) for at least a minute on the tritium channel. The counts in each sample will peak, and then slowly decline.

Each assay mixture, as just described, was made up individually immediately before adding the sample containing luciferase enzyme (step 5 above) and placing in the counter. The time between adding the sample and starting the counter was standardized as much as possible.

EXAMPLE 5

Construction of pSV2lux and Its Use in Animal Cells

A. Preparation of Plasmid pSV2-β-globin DNA

Plasmid pSV2-β-globin was used as the starting material for construction of a vector which would drive expression of the present invention in animal cells. Plasmid pSV2-β-globin has been deposited with NRRL and is available under accession number NRRL B-15928. Plasmid pSV2-β-globin DNA was prepared in substantial accordance with the procedure of Example 1A.

B. Construction of Plasmid pSV2HNXB

A polylinker sequence was substituted for the β-globin gene in plasmid pSV2-β-globin to create plasmid pSV2HNXB. Fifteen μg of pSV2 -β-globin were digested with 20 μl of BglII and 25 μl of HindIII in a 100 μl reaction containing BRL core buffer (50 mM Tris-HCl, pH=8.0; 10 mM MgCl2; 50 mM NaCl). The reaction was incubated at 37° C. The DNA was purified in substantial accordance with the procedure of Example 2B. The DNA was resuspended in 150 μl TE buffer.

A synthetic double stranded DNA oligonucleotide was prepared on an Applied Biosystems Model 380A DNA synthesizer (Applied Biosystems, Inc., 850 Lincoln Center Drive, Foster City, Calif. 94404) according to the manufacturers recommendations. Many DNA synthesizing instruments are known in the art and can be used to make the oligonucleotides. In addition, the oligonucleotides can be conveniently prepared in substantial accordance with the procedures of Itakura et al., 1977, Science 198:1056 and Crea et al., 1978, Proc. Natl. Acad. Sci. USA 75:5765. The synthetic oligonucleotide had the sequence

Figure 10:
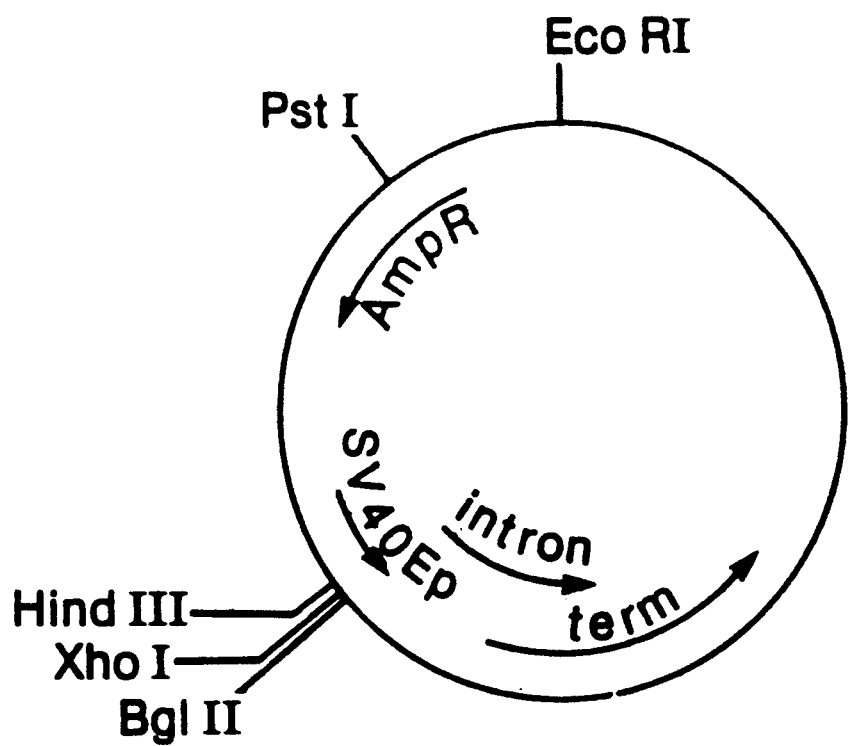
FIG. 10 shows the restriction site and function map of plasmid pSV2lux.

This oligonucleotide was kinased and annealed in substantial accordance with the procedure of Example 3G. One hundred ng of the digested DNA was ligated to 3 μg of synthetic polylinker in 10 μl NEB ligation buffer (50 mM Tris-HCl, pH=7.8; 10 mM MgCl2; 20 mM DTT; 50 μg/ml BSA) containing 1 mM ATP and 400 μl T4 DNA ligase (New England Biolabs). After a 48 hour incubation at 16° C., 5 μl of the ligation mixture was used to transform competent HB101 E. coli cells in substantial accordance with the procedure of Example 2G. The resulting colonies were screened by conventional minilysate analysis (Maniatis et al., supra, pages 365-370) using HindIII/BglII and XhoI/BamHI to confirm the presence of the polylinker and the absence of the β-globin gene. A restriction site and function map of the desired plasmid, designated pSV2HNXB, is shown in FIG. 10.

C. Construction of Plasmid pSV2lux

Ten μg of plasmid pSV2HNXB were digested with restriction enzymes, BglII and HindIII, in substantial accordance with the procedure of Example 2B, except that BglII (16U) and HindIII (20U) were substituted for BamHI and 10×BglII buffer. (10×BglII buffer=50 mM Tris-HCl, pH=7.5; 50 mM NaCl; 10 mM MglC2; 1 mM DTT was used instead of 10×BamHI buffer. The BglII and HindII digested pSV2HNXB DNA was then treated with CIAP in substantial accordance with the procedure of Example 4B. The dephophorylated DNA was purified in substantial accordance with the procedure of Example 2B, and resuspended in 25 μl of TE buffer.

The luxAB gene was isolated from plasmid pIT20 on an ~2.4 kb HindIII/XhoII fragment as described in Example 2 (2E and 2F). One μl (~125 ng) of the luxAB containing HindIII-XhoII fragment was mixed with 1 μl (~10 ng) of the BglII-HindIII cleaved and CIAP treated pSV2HNXB DNA, and the fragments were ligated in substantial accordance with the procedure of Example 2G.

The ligation mixture (~2 μl) was transformed into competent cells of E. coli strain AG-1 available from Stratagene (11099 N. Torrey Pines Rd., La Jolla, Calif. 92037) AG-1 cells are a high efficiency variant of E. coli DH1 cells with the following genotype: F-, endA1, hsdR17 (rK−,mK+), supE44, thi-1, λ-,recA1, gyrA96, relA1. Transformation with AG-1 cells was accomplished in substantial accordance with the manufacturer's directions as follows. The frozen competent cells are thawed on ice. For each transformation a 100 μl of the thawed bacterial suspension is used.

Five μl of beta-mercaptoethanol is added to the 100 μl aliquot of cells, with gentle swirling, and the cells are put on ice for 10 minutes, with gentle swirling every 2 minutes. The DNA (1-5 μl) is added to the cells and the mixture is incubated on ice for 30 minutes. (Highest efficiencies are observed when less than 1 ng of DNA is added per 100 μl of cells). The mixture is placed in a 42° C. H2O bath for 45 seconds and then allowed to sit on ice for 2 minutes. Then, 0.9 ml of SOC medium [SOC medium=20 g/l bacto tryptone, 5 g/l yeast extract, 10 mM NaCl, 2.5 mM KCl; after autoclaving add 10 ml/l of a magnesium solution (1 M MgCl2—1 M MgSO4 sterilized by filtration) and 10 ml/l of a 2 M glucose solution (sterilized by filtration); then the complete SOC medium is filter sterilized again] is added, followed by incubation at 37° C. for 1 hour with shaking at 225 rpm. Following this incubation, cells may be plated directly, 200 μl or less per plate, or they may be concentrated by centrifuging at 1000 rpm for 10 minutes. After centrifugation, the pellet is then resuspended in 200 μl and plated on a 100 mm plate. When plating only several μl, the transformation mix is added to 200 μl of SOB medium [SOB medium=same as SOC medium but without 10 ml/l of 2 M glucose solution] and plated on LM agar plates [LM agar=10 g/l bacto tryptone, 5 g/l yeast extract, 10 g/l NaCl, 15 g/l bacto agar; after autoclaving, add 10 ml of sterile 1 M MgSO$_4$ and appropriate antibiotic when temperature drops below 55° C. (omit MgSO$_4$ for tetracycline plates)].

Figure 11:
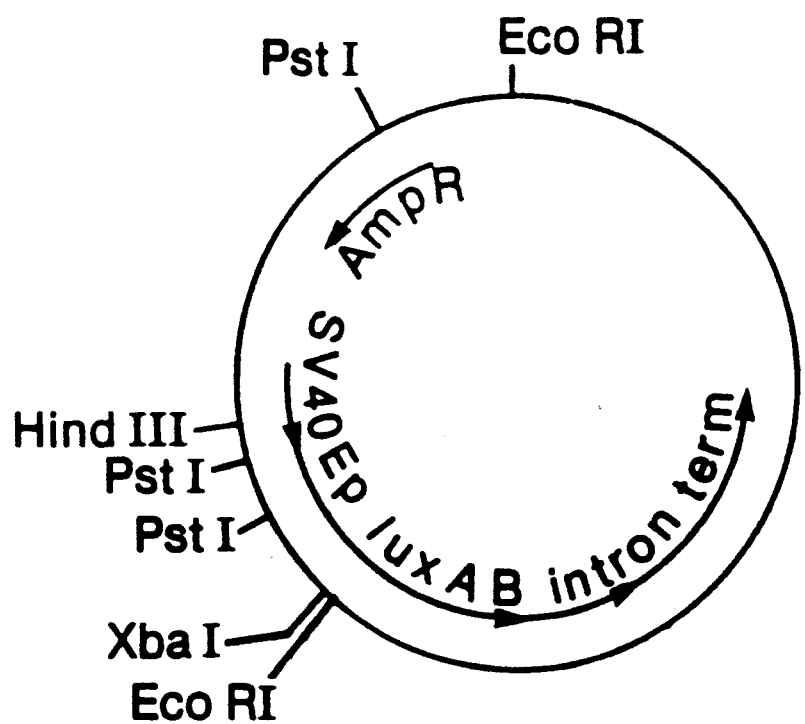
FIG. 11 shows the restriction site and function map of plasmid pSV2lux.
Figure 12:
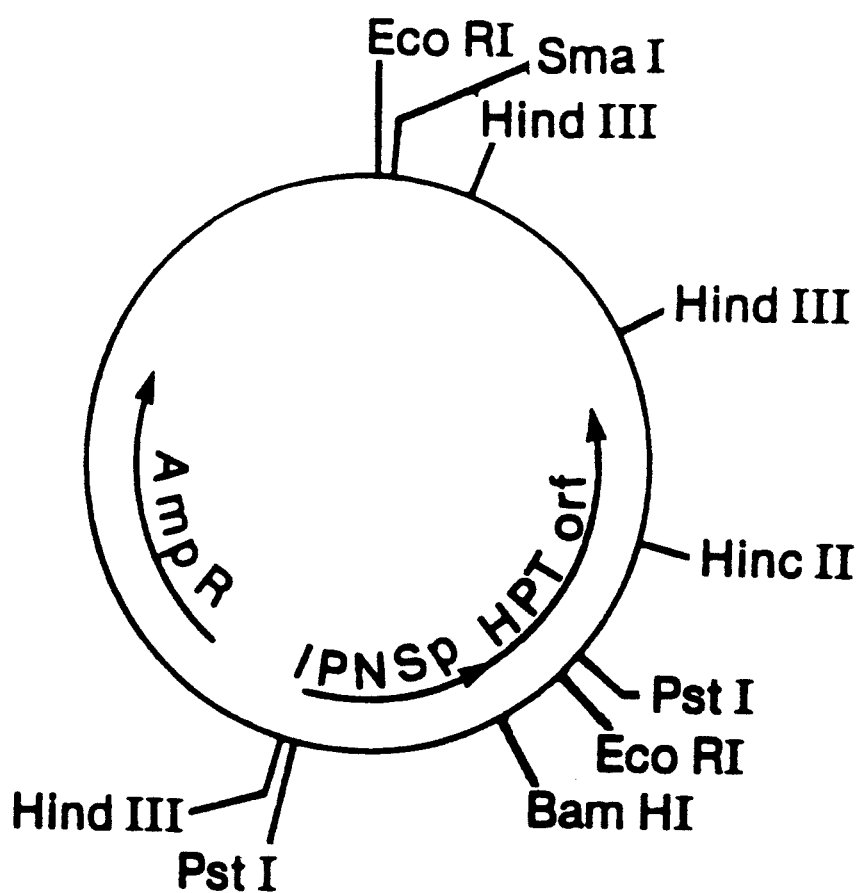
FIG. 12 shows the restriction site and function map of plasmid pPS29.

The resulting transformant colonies were screened by conventional minilysate analysis, as described in Example 5B above, to confirm the luxAB insert. A restriction site and function map of the desired plasmid, designated pSV2lux, is shown in FIG. 11.

D. Transfection of pSV2lux into COS-1 Cells

Although the following procedure describes the construction of COS-1/pSV2lux transfectants, it is equally applicable for the construction of COS-1 transformants of other pSV2 derived plasmids. Furthermore, the procedure given in generally applicable to a variety of mammalian cell lines. Transfection procedures for mammalian host cells are well known in the art, i.e., Wigler et al., 1979, P.N.A.S. USA 76:1373; Graham et al., 1973 Virology 52:456; Ausubel et al., (eds.), 1987, Chapter 9 in *Current Protocols in Molecular Biology*, Greene/Wiley Interscience, New York.

1. Preparation of the Cells

A culture of COS-1 cells, (ATCC CRL-1650) is passaged one to two days prior to the transformation, so as to provide 40–50% confluency on the day of the transformation. The media is changed two to three hours before the transformation. One 25 cm$^2$ flask of cells is needed for each transformation.

2. Preparation of the DNA

Ten to twenty μg of plasmid pSV2lux DNA are added to 62.5 μl of 2 M CaCl$_2$ and 437.5 μl of H$_2$O. The 0.5 ml of DNA is then added dropwise to 0.5 ml of 2×HeBS (10 g/l Hepes, pH=7.5; 16 g/l NaCl; 0.74 g/l KCl; 0.25 g/l Na$_2$PO$_4$; and 2 g/l dextrose), forming a milky precipitate. The mixture is allowed to stand for 10–20 minutes at room temperature before it is added to the cells. A longer incubation time may result in a coarser precipitate that does not transform well, but sometimes a longer incubation time may be necessary to form a precipitate.

3. Transfection of the Cells

The 1 ml DNA solution prepared in part 2 above is added to a 25 cm$^2$ flask of COS-1 cells with gentle agitation and incubated at 37° C. for 3–4 hours. The cells are washed twice with serum-free growth media (Dulbecco's Modified Eagle Medium (DMEM), Gibco).

Transfection efficiency may be increased with certain cell lines by a "glycerol-shock" treatment as follows. One ml of HeBS with 15% glycerol is added to the cells, which are then incubated at 37° C. for two minutes. The "glycerol-shock" incubation is terminated by the addition of serum-free growth media, followed by two washes with serum-free growth media. Complete fresh growth media containing 10% fetal bovine serum is added and the cells are grown for 48 hours, harvested by centrifugation, and then frozen in a dry ice-ethanol bath.

E. Determination of LuxAB Gene Product Activity in Mammalian Cells

Extracts of COS-1/pSV2lux cells (see Example 5D) are prepared by three freeze-thaw cycles. Cells are suspended in 1×plant grinding buffer (Example 4E), frozen in a dry ice-ethanol bath, then thawed at 37° C. This process is repeated two more times, after which the suspension is centrifuged at 13,000×g for 5 minutes. The supernatant is then assayed for luciferase enzyme activity in substantial accordance with the procedure of Example 4F.

EXAMPLE 6

Construction of pIT22 and Its Use in Cephalosporium acremonium Cells

A. Isolation of Plasmid pPS29

Plasmid pPS29 contains the bacterial hygromycin B phosphotransferase gene fused to the isopenicillin N synthetase (IPNS) gene promoter from *C. acremonium*. Construction and preparation of plasmid pPS29 DNA has been described previously in U.S. patent application Ser. No. 06/895,008, filed Aug. 8, 1986, which is hereby incorporated by reference.

B. Construction of Plasmid pIT2

To facilitate the final construction of pIT22 which contains the LuxAB gene fused to the *C. acremonium* isopenicillin N synthetase promoter, it was helpful to insert a BglII site into pPS29. This was accomplished by digesting pPS29 with restriction enzyme XmaI, which cuts only once in the plasmid, and inserting a synthesized DNA linker as described below.

Approximately 20 μg of pPS29 DNA was suspended in 170 μl of H$_2$O, and 20 μl of 10×XmaI buffer were added (10×XmaI buffer=0.5 M NaCl, 0.06 M Tris-HCl, pH=7.5, 0.06 M MgCl$_2$, and 0.06 M beta-mercaptoethanol). Ten μl (~10 units) of restriction enzyme XmaI were added and the mixture was incubated at 37° C. for 2 hours, at which time 10 more units XmaI were added and the digestion was continued an additional 2 hours. The DNA was then purified in substantial accordance with the procedure of Example 2B.

Two single stranded synthetic linkers were then synthesized, purified, kinased and annealed in substantial accordance with the procedure of Example 5B. The linker had the sequence:

Gk1: 5'-CCGGAGATCTAGA-3'
Gk2: 5'-CCGGTCTAGATCT-3'.

Figure 13:
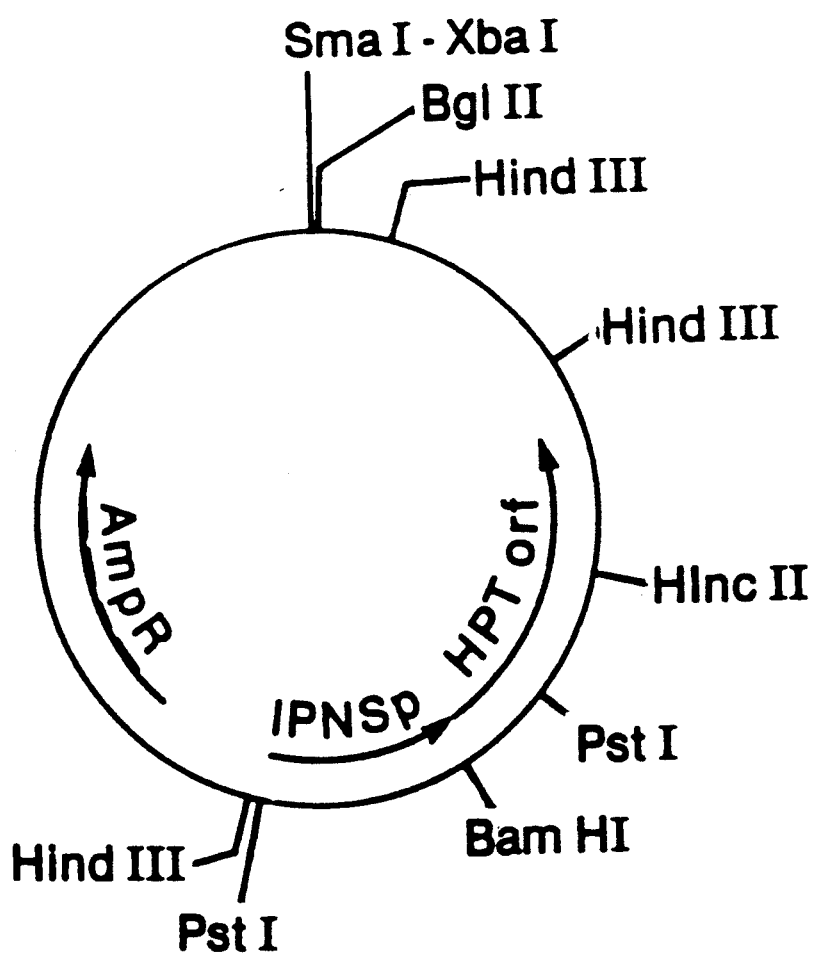
FIG. 13 shows the restriction site and function map of plasmid pIT2.
Figure 14:
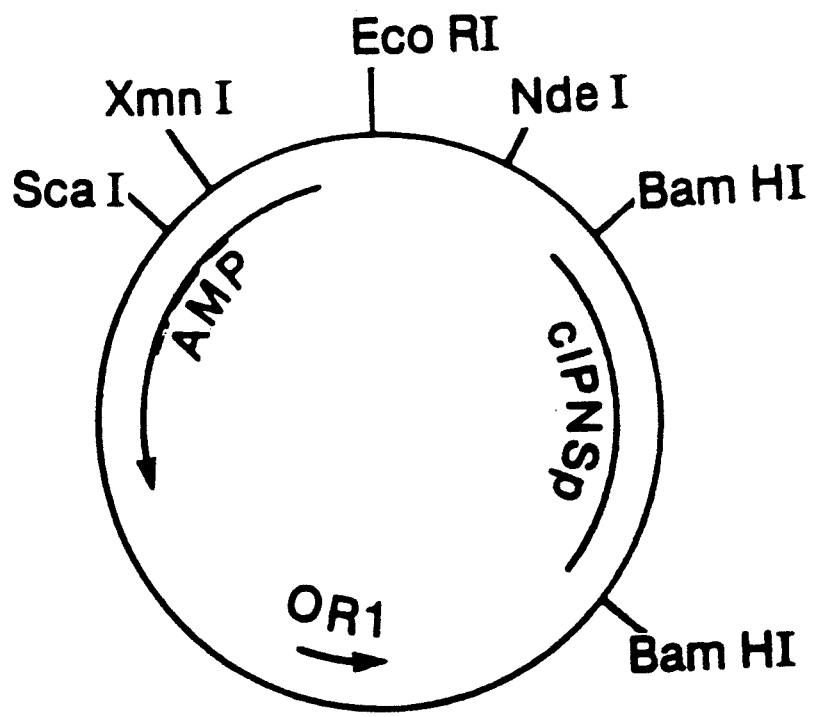
FIG. 14 shows the restriction site and function map of plasmid pPS23.

Approximately one μg of the XmaI digested pPS29 was mixed with ~10 pmoles of kinased, annealed Gk1:Gk2 linker. The mixture was ligated, transformed into *E. coli* K12 JM109 cells, and recombinant plasmid was characterized from transformants in substantial accordance with the procedure of Example 2G. The desired plasmid containing unique XmaI and BglII restriction sites, designated pIT3, was identified and prepared in substantial accordance with the procedure of Example 1A. A restriction site and function map of pIT2 is shown in FIG. 13.

C. Isolation of the *C. acremonium* IPNS promoter from pPS23

The *C. acremonium* IPNS promoter was isolated from pPS23. Construction of pPS23 has been described in U.S. patent application Ser. No. 06/895,008, filed Aug. 8, 1986. The desired ~650 bp BamHI-PstI fragment is isolated from pPS23 in substantial accordance with the procedure of Example 2F. A HindIII restriction site was placed in the 5' noncoding region of the *C. acremonium* IPNS gene in order to facilitate fusion of the *C. acremonium* IPNS promoter to the LuxAB gene, as described below in sections D-G of this Example.

D. Preparation of BamHI- and PstI-Digested Vector M13mp18

About 2.5 μg of phage M13mp18 DNA (available from New England Biolabs) was digested in 100 μl of 1×BamHI buffer with 1 μl each (~20 units each) of restriction enzymes BamHI and PstI for 90 minutes at 37° C. The reaction mixture was extracted with phenol:CHCl$_3$ and the DNA, in the aqueous phase, concentrated by ethanol preciptation. The DNA pellet was resuspended in 20 μl of 0.1×TE buffer and constituted ~2 82 g of the desired BamHI-and PstI-digested M13mp18 vector. The vector DNA obtained was stored at −20° C.

E. Construction of Phase mIT21

One μg of the ~650 bp BamHI-PstI fragment containing the *C. acremonium* IPNS promoter, described in Example 6C, and 1 μl of BamHI- and PstI-digested vector M13mp18 are ligated in a 20 μl reaction containing the DNA fragments, 2 μl of 10×ligase buffer (0.5 M Tris-HCl, pH=7.5, and 100 mM MgCl$_2$), 2 μl of 5 mM ATP, 1 μl of 6 μg/μl BSA, 12 μl of glass-distilled H$_2$O, and 1 μl (1 Wales unit) of T4 DNA ligase (Boehringer Mannheim Biochemicals). The reaction is incubated ~18 hours at 15° C. The ligated DNA constitutes the desired phage mIT21 along with other ligation products.

F. Transformation of *E. coli* K12 JM109 With Phage mIT21

Competent *E. coli* K12 DH5αF' were purchased from Bethesda Research Laboratories (P.O. Box 6009, Gaithersburg, Md. 20877) and transformed with a ligation reaction constituting phase mIT21 (described in Example 6E) in substantial accordance with the manufacturer's directions, except that the DNA was in a volume of 20 μl and no dilution into medium or expression time was necessary. Post-transformation, the cells were distributed in ~1, 10, 20, 40 and 50 μl aliquots to 13×100 mm sterile glass tubes containing 0.25 ml/tube *E. coli* K12 DH5αF' in logarithmic growth phase. To these tubes were added 3 ml of top agar [L broth (10 g/l bacto tryptone, 5 g/l bacto yeast extract, 10 g/l NaCl) with 0.8% agar kept molten at 45° C]. The cell-top agar mixture was then plated on L-agar (L broth with 15 g/l agar) plates containing 40 μg/ml 5-bromo-4-chloro-3-indolyl-β-D-galactoside (X-gal) and 0.1 M isopropylthio-β-galactoside (IPTG), and the plates were incubated at 37° C. overnight. (Detailed descriptions of M13 procedures were found in the M13 *Cloning/Dideoxy Sequencing Instruction Manual,* Bethesda Research Laboratories (BRL), Life Technologies, Inc., Gaithersburg, Md. 20877). Transformants are identified by insertional inactivation of β-galactosidase activity (colorless plaque phenotype) and restriction enzyme analysis of replicative form (RF) DNA. For screening purposes, clear plaques are plugged from the plate overlay with a Pasteur pipette into 3 ml per plaque of early logarithmic growth phase *E. coli* K12 KH560 F'. Cultures are incubated from 6 to 18 hours at 37° C. with aeration.

Following this incubation, 1.5 ml of each culture are pelleted in separate 1.5 ml Eppendorf tubes. The supernatants are decanted into fresh tubes and stored at 4° C. to serve as a source of phage inoculum. Replicative form DNA is prepared from the cell pellets in substantial accordance with the teaching of the alkaline plasmid preparation procedure of Birnboim and Doly, 1979, Nuc. Acid Res. 7(6):1513-1523, with the following exceptions. The procedure is scaled up such that 1.5×volumes of Solutions I, II, and III are used, and the cleared lysate is extracted once with an equal volume of CHCl$_3$. The DNA is then precipitated by the addition of 0.4 volumes of isopropanol and incubation at room temperature for 20 minutes. The DNA is collected by centrifugation and then precipitated with ethanol out of 0.3 M NaOAc. The analysis of the restriction pattern of the RF DNA is facilitated by the existence of an asymmetric XhoI restriction enzyme recognition site that is not only diagnostic for the presence of the desired insert but also can be used to orient the insert sequence relative to the multiple-cloning site (MCS) of the M13 vector.

G. Preparation of Single-Stranded Phase mIT21 DNA

A 10 ml culture of early logarithmic growth phase *E. coli* K12 DH5αF' was inoculated with ~200 μl of phase stock (prepared in Example 6E) and incubated ~18 hours at 37° C. with aeration. The culture was centrifuged and the resulting supernatant transferred to a new tube and centrifuged again. The supernatant was again decanted to a fresh tube. One ml of a solution of 25% polyethylene glycol (molecular weight of −3,350) in 3 M NaCl was added to the supernatant, which was then incubated for 15 minutes at room temperature. The resulting mixture was centrifuged for 30 minutes at 10,000 rpm in a JA-14 rotor (Beckman). The pellet obtained by the centrifugation contained the single-stranded phase mIT21 and was resuspended in 400 μl of TE buffer. The solution was extracted first with CHCl$_3$ and then with TE-saturated phenol. The phenol was allowed to stay in contact with the aqueous phage for 15 minutes. The solution was then extracted twice with a mixture of TE-saturated phenol:CHCl$_3$ (1:1, v/v), and twice with CHCl$_3$ alone. The DNA was then precipitated out of 0.3 M NaOAc. The DNA was collected by centrifugation, and the pellet was resuspended in 100 μl of 0.1×TE buffer. This solution constituted ~5 μg of single-stranded phase mIT21 DNA.

H. Site-Directed Mutagenesis to Construct Phase mIT22

The single-stranded DNA fragment used in the mutagenesis (and subsequent hybridizations to detect desired phages) was synthesized on an automated DNA synthesizer in substantial accordance with the procedure of Example 5B. The M13 universal primer (a 15-mer), was purchased from BRL. The mutagenesis fragment synthesized was a single-stranded DNA that was 33 nucleotides in length and identical to the IPNS promoter sequence in phage mIT21 except for four bases. The 4 base mismatch (underline) will create a restriction enzyme HindIII recognition sequence at about position 1 of the IPNS coding sequence, with the DNA sequence:

HindIII
5'-GACAAACCGTCACCAAGCTTAAGGATCCGGCCC-3'

The 5' ends of about 100 pmoles of the 33 nucleotide single-stranded fragment were phosphorylated (kinased) in a reaction mixture containing single-stranded DNA at a concentration of 1 pmole/μl, 10 μl of 10×ligase buffer, 1000 pmoles adenosine triphosphate (ATP), 10 μl of 0.1 M DTT, 65 82 1 of glass-distilled H$_2$O, and 1 μl (10 Richardson units) of T4 polynucleotide kinase (Boehringer Mannheim Biochemicals). The reaction mixture was incubated at 37° C. for 30 minutes, at which time an additional 1 μl of kinase enzyme was added. The reaction mixture was then incubated for another 30 minutes at 37° C. and then quenched by incubation at 68° C. for 5 minutes.

The 5' ends of about 40 pmoles of M13 universal primer were kinased in an analogous 40 μl of reaction mixture containing the same amount of kinase enzyme.

The single-stranded phage mIT21 DNA was mutagenized in substantial accordance with the teaching of Adelman et al., 1983, DNA 2(3):183-193 as described below. The annealing reaction was carried out by adding ~500 ng (in 15 μl of 0.1×TE buffer) of single-stranded phase mIT21 DNA to 8 μl of 10×annealing buffer (100 mM Tris-HCl, pH=7.5; 1 mM EDTA; and 500 mM NaCl), 4 μl (~4 pmoles) of kinased 33 base fragment, 4 μl (~4 pmoles) of kinased M13 universal sequencing primer, and 50 μl H$_2$O, incubating the mixture at 80° C. for 2 minutes, then at 55° C. for 5 minutes, and finally at room temperature for 5 minutes.

The extension reaction was carried out by adding 120 μl of the following mixture to the solution of annealed DNA: 20 μl 10×Klenow-ligase buffer (100 mM Tris-HCl, pH=7.5; 1 mM EDTA; and 500 mM NaCl), 20 μl of 0.1 M DTT; 20 μl of a solution 6.25 mM in each of dGTP, dATP, dTTP, and dCTP; 20 μl of 5 mM ATP; 120 μl of H$_2$O; and 2.5 μl (~12.5 units) of Klenow enzyme (Boehringer Mannheim Biochemicals). The extension reaction mixture was incubated at room temperature for 1 hour, then at 37° C. for 4 hours, and finally at 14° C. for ~18 hours.

The extension reaction was extracted once with CHCl$_3$ and the DNA precipitated with ethanol and NaOAc and collected by centrifugation. The DNA pellet was resuspended in 400 μl 1×S1 buffer (0.3 M NaCl and 3 mM ZnOAc). Half the DNA solution was held in reserve at −20° C.; half was aliquoted to five 1.5 ml tubes. To four of these tubes was added 1 μl of S1 nuclease (Boehringer Mannheim Biochemicals) that had been diluted to 200 30-minute units per μl. The reactions were incubated at room temperature for 5, 10, 15, and 20 minutes, respectively. The reactions were stopped by first adding 5–10 μg of tRNA to the reaction mixture to serve as carrier, then extracting with a TE-saturated phenol-CHCl$_3$ mixture (1:1, v/v). The sample that was not treated with S1 nuclease (the negative control) was also extracted. The DNA in the aqueous phase was concentrated by ethanol precipitation and collected by centrifugation. The DNA pellets were each resuspended in 20 μl H$_2$O.

Ten μl of each of the resulting S1-treated DNA solutions were used to transform E. coli K12 DH5αF' cells in substantial accordance with the procedure described in Example 3F, except that the plates did not contain either X-Gal or IPTG. Desired mutants were identified by restriction enzyme digestion of double stranded phage RF DNA. Phage containing an extra HindIII restriction site were characterized further by DNA sequencing. An isolate containing the desired sequence was identified and designated mIT22. The mIT22 double stranded RF DNA was prepared in substantial accordance with the procedure of Example 6F.

I. Construction of Plasmid pIT30

Although the RF DNA of phage mIT22 contains the IPNS promoter sequence on the XmaI-HindIII restriction fragment which could be utilized in the construction of the E. coli C. acremonium shuttle vector pIT22, it is sometimes difficult to accumulate the RF of mIT21 in sufficient quantity for fragment isolation. To facilitate the construction of plasmid pIT22, the intermediate plasmid pIT30 was constructed. Plasmid pIT30 DNA was then utilized as a source of the IPNS promoter sequence to construct pIT22 as described in Example 6J below.

Replicative form DNA from E. coli K12 DH5αF' cells infected with phage mIT22 was isolated in substantial accordance with the procedure described in Example 6F. About 2 μg of the RF DNA of phage mIT22 were digested with restriction enzyme PstI (~10 units) in a reaction containing the DNA in 1×BamHI buffer. After incubation for ~90 minutes at 37° C., restriction enzyme HindIII (~10 units) was added and the reaction mixture was incubated a further 90 minutes. The reaction mixture was then extracted with CHCl$_3$ and the DNA concentrated by precipitation with ethanol and NaOAc. The DNA was collected by centrifugation and the pellet resuspended in 10 μl of H$_2$O.

PstI- and HindIII-digested plasmid pUC18 DNA (available from New England Biolabs) was prepared in substantial accordance with the procedure described in Example 2B.

Figure 15:
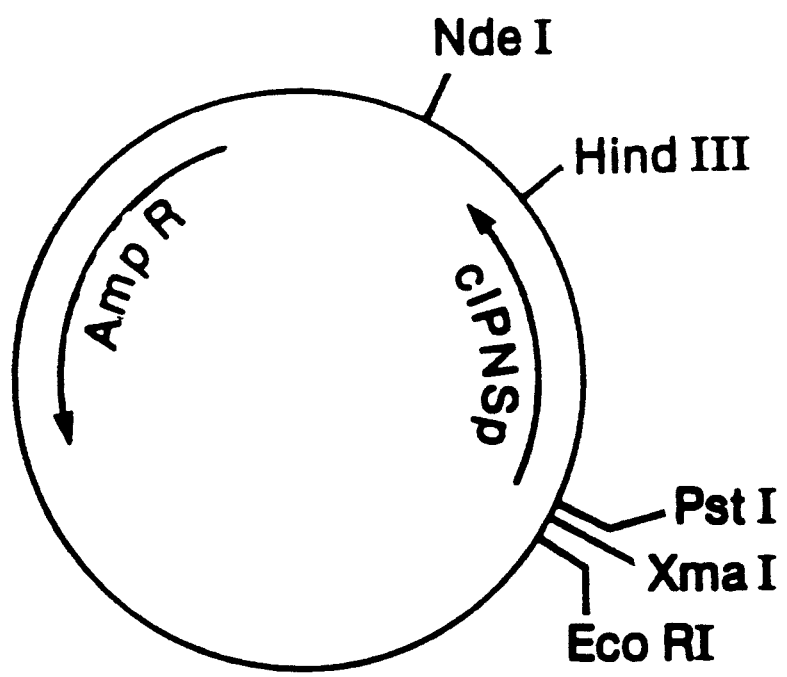
FIG. 15 shows the restriction site and function map of plasmid pIT30.

Five μl (~1 μg) of PstI- and HindIII-digested phage mIT22 DNA and 1 μl (~100 ng) of PstI and HindIII-digested plasmid pUC18 DNA were ligated in substantial accordance with the procedure described in Example 2G. The ligated DNA constituted the desired plasmid pIT30 along with other ligation products. A restriction site and function map of plasmid pIT30 is presented in FIG. 15 of the accompanying drawings.

The ligation reaction constituting the desired plasmid pIT30 was transformed into competent E. coli K12 JM109 (Stratagene) in substantial accordance with the manufacturer's protocol (as described in Example 5C) except that 1 ml of L broth was used for dilution. Aliquots of the transformation mixture were plated on L-agar plates containing ampicillin (100 μg/ml), X-gal (40 μg/ml), and IPTG (0.1 M). Plates were incubated at 37° C. for ~18 hours. Desired transformants were identified by their ampicillin-resistant phenotype and white colony color (due to insertional inactivation of β-galactosidase) and by restriction enzyme analysis of their plasmid DNA. Plasmid DNA was prepared from 3 ml cultures in substantial accordance with the procedure described in Example 6F for preparing RF DNA from phage M13-infected E. coli K12 JM109 cell pellets. Plasmid DNA from one transformant was prepared in substantial accordance with the procedure described in Example 1A for use in subsequent constructions.

J. Construction of Plasmid pIT22

Plasmid pIT22 was constructed by ligating together the following three DNA restriction fragments; (1) the ~650 bp XmaI-HindIII restriction fragment from plasmid pIT30 that contains the *C. acremonium* IPNS promoter sequence; (2) that ~2.4 kb HindIII-XhoII fragment from plasmid pIT20 which contains the LuxAB gene; and (3) the ~6.1 kb XmaI-BglII fragment from plasmid pIT2 containing the sequences required for maintenance and selection in *E. coli* and *C. acremonium*.

Approximately 20 μg of pIT30 DNA were suspended in 170 μl total volume of H$_2$O, and 20 μl of 10×22 XmaI buffer was added. XmaI digestion was carried out as described for pPS29 DNA in Example 6B. The DNA was purified and then digested with HindIII in substantial accordance with the procedure of Example 2B. The desired ~650 bp XmaI-HindIII fragment was purified from a 6% acrylamide gel and purified as described in Example 3D. Plasmid pIT2 was digested with XmaI and BglII as described above for pIT30 except that pIT2 DNA was substituted for pIT30 DNA and restriction enzyme BglII was substituted for HindIII. The digested DNA was purified from an agarose gel as described in Example 2F.

Purification of the HindIII-XhoII fragment of pIT20 containing the LuxAB gene has been described previously in Example 2F.

Figure 16:
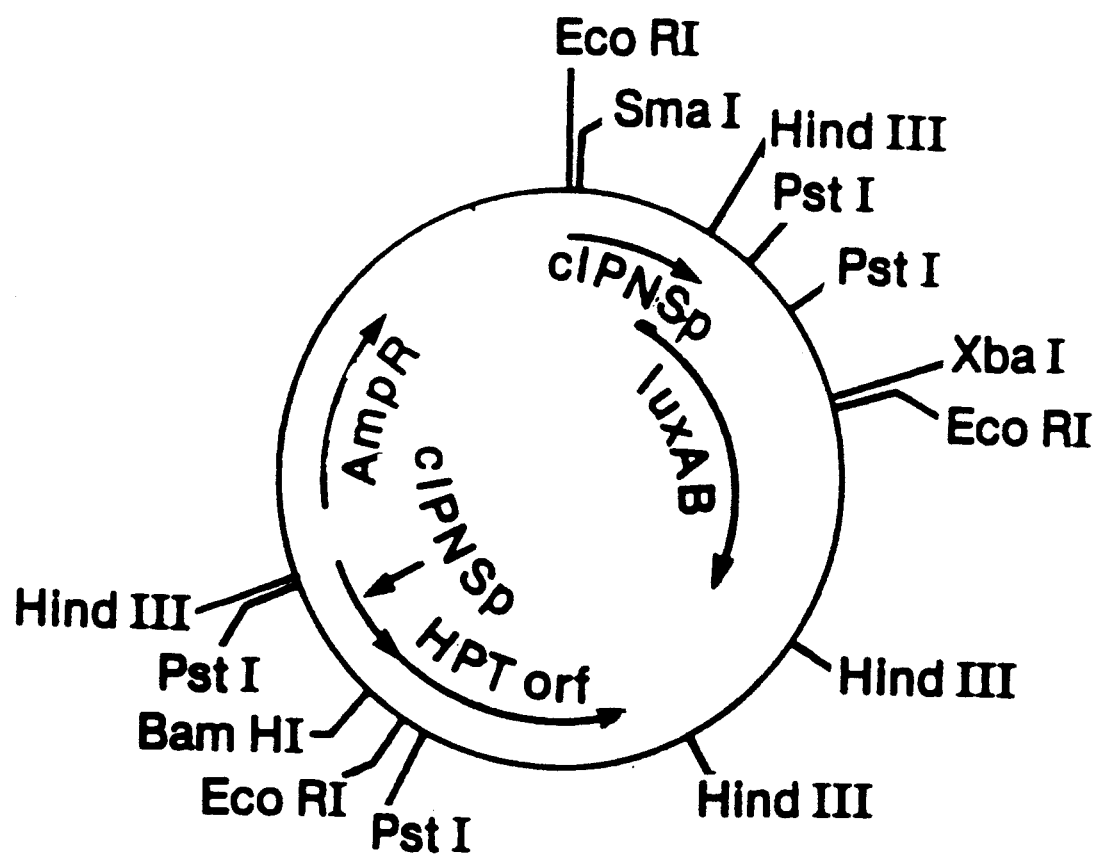
FIG. 16 shows the restriction site and function map of plasmid pIT22.

One μg of the ~650 bp XmaI-HindIII reaction fragment of pIT30, one μg of the ~6.1 kb XmaI-BglII restriction fragment of pIT2, and one μg of the ~2.4 kb XhoII-HindIII fragment of pIT20 were mixed and ligated as described in Example 2G. The ligation mixture was transformed into *E. coli* K12 DH5αF', and DNA from transformants was screened for the desired electrophoretic pattern after digestion with restriction enzyme HindIII. DNA from the desired plasmid, designated pIT22, was prepared as described in Example 1A. A restriction site and function map of pIT22 is shown in FIG. 16 of the accompanying drawings.

K. Transformation of *Cephalosporium acremonium* with Plasmid pIT22

U.S. Pat. No. 4,762,786 discloses and claims the following transformation procedure.

1. *Cephalosporium acremonium* Strains

The preferred Cephalosporium strain for transformation is obtained from the American Type Culture Collection under the accession number ATCC 11550. Other restrictionless Cephalosporium strains or any commercial strains derived from ATCC 11550 by mutation/selection of genetic breeding for the purpose of improved production of cephalosporin C are also suitable for use.

2. Preparation of Inoculum for Cell Culture

To genetically transform *C. acremonium* cells efficiently, it is necessary to remove the cell walls and form stable protoplasts. In the preparation of such protoplasts, it is highly advantageous to begin with a uniform incoculum. Otherwise, preparation of cells in culture is not reproducible and time is lost by attempts to prepare *C. acremonium* protoplasts from unsuitable or inadequate amounts of cells.

3. Preparation of Uniform Inoculum for Cell Culture

An ampoule of spores (approximately 10$^9$ conidia in 1.5 ml of preservation menstrum: 5% lactose, 10% glycerol, and 0.1% Tween 80) is taken from liquid nitrogen storage, thawed at room temperature and diluted in 5 ml of sterile saline. About 0.1 ml is used to inoculate each of approximately 50 slants containing 20 ml of Trypticase-Soy Agar (BBL) medium. Before inoculation, the medium is allowed to dry until surface moisture is no longer visible. Inoculated slants are incubated for about four days at 25° C. About 10 ml of preservation menstrum are added to the mycelial growth which covers the surface of the medium in each slant. The slants are vortexed to suspend the conidia and the conidial suspension from each slant is pooled and 10 ml aliquots frozen at −80° C. The frozen conidial suspension slowly loses viability and should not be used after about three months of storage at −80° C.

4. Growth of Cells for Preparation of Protoplasts

Approximately 106 ml of aqueous medium in a 500 ml shake flask is inoculated with cells from the 10 ml of frozen conidial suspension. Cells are obtained by centrifugation (10 min×2600 rpm), and then directly suspended in the aqueous culture medium. Aqueous culture medium was prepared as follows: 100 ml of solution A (Sucrose, 36 g/l; L-asparagine, 7.5 g/l; KH$_2$PO$_4$, 15 g/l; K$_2$HPO$_4$, 21 g/l; Na$_2$SO$_4$, 0.75 g/l, MgSO$_4$, 7 H$_2$O; 0.18 g/l; CaCl$_2$, 0.06 g/l; salts solution, 1 ml/L; natural pH. Salts solution: Fe(NH$_4$)(SO$_4$)$_2$.6 H$_2$O, 15 g/l; MmSO$_4$.4 H$_2$O, 3 g/l; ZnSO$_4$.7 H$_2$O, 3 g/l; CuSO$_4$.5 H$_2$O, 0.8 g/l) is dispensed into a 500 ml shake flask; the flask is covered with a commercial closure and is autoclaved at 121° C. for 20 minutes. Two ml of solution B (Glucose 108 g/l (autoclaved at 121° C. 30 minutes)) and 4 ml of solution C (Sucrose 25 g/l; corn steep liquor, 4% nitrogen (w/v), 12.5 ml; ammonium acetate, 5.5 g/l; CaCO$_3$, 5 g/l; pH adjusted to 6.5 with KOH; autoclaved at 121° C. for 20 minutes). Decantation of the supernatant is necessary prior to suspension because the lactose and glycerol adversely affect the growth of cells. The flask containing the suspended cells is placed on a gyratory H$_2$O bath shaker and incubated 24 hours at 285 rpm with a 1 inch throw at 29°-30° C. It is important to observe the recommended temperature of 29°-30° C. in the culturing step to obtain cells suitable for preparing transformable protoplasts. However lower temperatures of about 25° C. are also suitable. Those familiar with the art will recognize that the 29°-30° C. is different from the temperature (25° C.) preferred for culturing *C. acremonium* for purposes of antibiotic production.

5. Preparation of Cephalosporium Protoplasts

Cells for a 24 hour culture are harvested by suction filtration (Whatman #1 paper in a Buchner funnel) and suspended in McIlvaine's Buffer, pH 7.1 (0.1 M citric acid, 0.2 M dibasic sodium phosphate) to which dithiothretiol has been added to a concentration of 0.01 M. Sufficient buffer is added to attain a final cell concentration of 1 g (weighed after suction filtration) of cell mass per 20 ml of buffer. The cell suspension is placed on a gyratory H$_2$O bath shaker in a 50 ml shake flask and incubated 90 minutes at 140 rpm with 1 inch throw at 29°-30° C. Dithiothreitol-treated cells are washed with H$_2$O and then resuspended in enzyme solution (25 mg/ml of β-glucuronidase-Sigma Chemical Company, in McIlvaine's buffer, pH 6.35; supplemented with 0.8 M NaCl and 0.02 M MgSO$_4$). The final cell concentration is 1 g of treated cell mass per 10 ml of enzyme solution. The cell suspension is then placed on a gyratory H$_2$O bath shaker and incubated for 3 hours at 120 rpm with 1 inch throw at 29°-30° C. The suspension of protoplasts is diluted with 4 volumes of washing solution (0.8 M NaCl and 0.02 M MgSO$_4$) and then gravity filtered through two layers of paper toweling. The filtrate containing the protoplasts is centrifuged for 5 minutes at 2600 rpm at room temperature. The supernatant is decanted and the pellet of protoplasts suspended in 10 ml of washing solution. After the washing procedure is repeated twice, the washed protoplasts are resuspended in sufficient 0.08 NaCl to achieve a concentration of 2 to 3×10$^8$ protoplasts per ml (hemacytometer count).

6. Transformation Procedure

To a 1 ml suspension of Cephalosporium protoplasts (2 to 3×10$^8$ per ml) in 0.08 M NaCl solution, 0.005 ml of freshly distilled DMSO and CaCl$_2$ to a final concentration of 80 mM are added followed by addition of about 1 to 20 micrograms of plasmid pIT22 DNA. Next, Polyethylene Glycol 4000 (Baker, >20% w/v in H$_2$O) is added to achieve a mixture with a volume of 10 ml. The mixture is incubated for 10 minutes at room temperature and then centrifuged at 700 rpm for 5 minutes followed by 2500 rpm for 10 minutes. The pellet of protoplasts is suspended in 1 ml of 0.08 M NaCl. Aliquots (0.1 ml) are delivered to the surface of Trypticase-Soy Agar medium (BBL) that has been enriched with 10.8% sucrose to osmotically stabilize the protoplasts. After the petri plates are incubated at 15° C. for 24 hours, 4 ml of liquified agar (0.41% w/v, at 42° C.) containing 0.8 M sodium chloride and sufficient hygromycin B to achieve a final concentration of 100 μg/ml are added to each petri dish. After the overlay has solidified, the petri plates are then incubated at 25° C in a humidified chamber. Although transformant colonies of sufficient size to subculture are present 12 days after transformation, slower growing transformants may take as long as 60 days. Abortive transformants are easily distinguished from stable transformants because abortants fail to grow upon subculture to fresh selective medium.

L. Determination of LuxAB Gene Product Activity in Cephalosporium acremonium Cells Extracts of C. acremonium/pIT22 cells (see Example 6K) are prepared by three freeze-thaw cycles. Cells are suspended in 1×plant grinding buffer (Example 4E), frozen in a dry ice-ethanol bath, then thawed at 37° C. This process is repeated two more times, after which the suspension is centrifuged at 13,000×g for 5 minutes. The supernatant is then assayed for luciferase enzyme activity is substantial accordance with the procedure of Example 4F.

We claim:
1. A recombinant DNA encoding a fusion protein having bacterial luciferase activity comprising operable linked in the 5' to 3' direction, the coding region of the luxA gene, a DNA linker, and the luxB gene, wherein the coding region of the luxA and the luxB genes are isolated from *Vibrio harveyi* and the DNA linker consists essentially of TCTAGA.
2. A fusion reporter gene that is luxAB.
3. A DNA cassette comprising a promoter operably linked to a fusion reporter gene of claim 2.
4. A plasmid vector comprising a fusion reporter gene of claim 2.
5. A plasmid vector that is pIT20.
6. A plasmid vector that is pIT24.
7. A plasmid vector that is pIT21.
8. A plasmid vector that is pGAR117.
9. A plasmid vector that is pSV2lux.
10. A plasmid vector that is pIT22.
11. A host cell transformed or transfected by the plasmid vector of claim 4.
12. A host cell transformed or transfected by the plasmid vector of claim 5.
13. A host cell transformed or transfected by the plasmid vector of claim 6.
14. A host cell transformed or transfected by the plasmid vector of claim 7.
15. A host cell transformed or transfected by the plasmid vector of claim 8.
16. A host cell transformed or transfected by the plasmid vector of claim 9.
17. A host cell transformed or transfected by the plasmid vector of claim 10.
18. A transformant that is *E. coli* K12 JA221/pIT20 (NRRL B-18301).
19. A transformant that is *E. coli* K12 JA221/pIT24.
20. A transformant that is *Sacchraromyces cerevisiae* DBY746/pIT21.
21. A transformant that is *Nicotiana plubmaginifolia*/pGAR117.
22. A DNA cassette of claim 1 which comprising the following elements 5' to 3', operably linked: a promoter DNA segment, a fusion reporter gene of claim 1.
23. A plasmid vector comprising the fusion reporter gene of claim 22.
24. A host cell transformed with the plasmid vector of claim 23.

* * * * *